(12) United States Patent
Matsumoto et al.

(10) Patent No.: US 7,719,687 B2
(45) Date of Patent: May 18, 2010

(54) APPARATUS FOR MEASURING REFLECTION CHARACTERISTICS OF OBJECT SURFACES

(75) Inventors: Jun Matsumoto, Yokohama (JP); Kenji Imura, Toyohashi (JP); Yoshihiro Okui, Daito (JP)

(73) Assignee: Konica Minolta Sensing, Inc., Sakai-shi (JP)

( * ) Notice: Subject to any disclaimer, the term of this patent is extended or adjusted under 35 U.S.C. 154(b) by 257 days.

(21) Appl. No.: 11/805,486

(22) Filed: May 23, 2007

(65) Prior Publication Data
US 2007/0273886 A1 Nov. 29, 2007

(30) Foreign Application Priority Data
May 23, 2006 (JP) ............................. 2006-142368

(51) Int. Cl.
*G01B 9/02* (2006.01)
(52) U.S. Cl. ...................................... 356/448; 356/630
(58) Field of Classification Search ......... 356/445–446, 356/402, 600–606, 448, 630; 250/228
See application file for complete search history.

(56) References Cited

U.S. PATENT DOCUMENTS

| | | | | |
|---|---|---|---|---|
| 5,963,328 A * | 10/1999 | Yoshida et al. | ............... | 356/600 |
| 6,088,117 A | 7/2000 | Imura et al. | ................. | 356/445 |
| 6,466,305 B1 * | 10/2002 | McBain | ...................... | 356/3.08 |
| 6,512,578 B1 * | 1/2003 | Komatsu et al. | .......... | 356/237.5 |
| 6,693,293 B2 * | 2/2004 | Oomori et al. | ............ | 250/559.4 |
| 7,006,229 B2 | 2/2006 | Sperling et al. | ............. | 356/445 |
| 7,391,518 B1 | 6/2008 | Schwarz et al. | ............. | 356/446 |
| 7,525,648 B2 * | 4/2009 | Sperling et al. | ............. | 356/226 |
| 2006/0187453 A1 | 8/2006 | Sperling | ..................... | 356/388 |
| 2006/0256341 A1 * | 11/2006 | Kuwada | ..................... | 356/445 |

FOREIGN PATENT DOCUMENTS

JP 8-29258 A 2/1996

(Continued)

OTHER PUBLICATIONS

Japanese "Notice of Reasons for Rejection" dated Sep. 30, 2008 for counterpart Japanese Application No. 2006-142368; Together with an English-language translation thereof.

(Continued)

*Primary Examiner*—Tarifur Chowdhury
*Assistant Examiner*—Michael Lapage
(74) *Attorney, Agent, or Firm*—Sidley Austin LLP

(57) ABSTRACT

A reflection characteristic measuring apparatus for measuring a characteristic, such as a gloss, of a sample surface. The apparatus includes at least one illuminator for illuminating a sample surface to be measured with light and a plurality of light receiving sections which are arranged axially symmetrically to each other with respect to a normal to an intended object surface and which output two-dimensional light receiving data. A deriving section derives a characteristic of the sample surface such as gloss based on a weighted average obtained by applying a weighting factor to each of the light receiving data outputted from the light receiving sections.

12 Claims, 14 Drawing Sheets

FOREIGN PATENT DOCUMENTS

| | | |
|---|---|---|
| JP | 2705842 B2 | 10/1997 |
| JP | 2001-41888 A | 2/2001 |
| JP | 2001-165772 A | 6/2001 |
| JP | 3243379 B2 | 10/2001 |
| JP | 2003-222594 A | 8/2003 |
| JP | 3555400 B2 | 5/2004 |
| JP | 2004-317131 A | 11/2004 |
| JP | 2005-9987 A | 1/2005 |

OTHER PUBLICATIONS

K. Imura, "4. measure color", Research for Textile end Uses, The Japan Research Association for Textile End-Uses, 1997, vol. 38, Sec. 4, pp. 191-199, 234; Together with Partial Translation.

"Specular Glossiness—Methods of Measurement", Japanese Industrial Standards Committee, JIS Z 8741-1997, Japan Standards Association, 1997; pp. 2-22; Together with Partial Translation.

* cited by examiner

APPARATUS FOR MEASURING REFLECTION CHARACTERISTICS OF OBJECT SURFACES

This application is based on Japanese Patent Application No. 2006-142368 filed on May 23, 2006, the contents of which are hereby incorporated by reference.

BACKGROUND OF THE INVENTION

1. Field of the Invention

The present invention relates to a reflection characteristic measuring apparatus for measuring a characteristic of a sample surface such as a gloss of the sample surface.

2. Description of the Related Art

There is known a reflection characteristic measuring apparatus for measuring the gloss of a sample surface. FIG. 18 is a diagram showing a construction of a conventional reflection characteristic measuring apparatus 100.

As shown in FIG. 18, the reflection characteristic measuring apparatus 100 includes an incident-side optical system 101 and a reflection-side optical system 102. The incident-side optical system 101 outputs light toward a sample surface S set in a proper position, with a certain angle with respect to the normal G passing a certain point on the sample surface S. The reflected light from the sample surface S is incident onto the reflection-side optical system 102 disposed at a position with a certain angle with respect to the normal G.

The incident-side optical system 101 and the reflection-side optical system 102 have diaphragms 103 and 104, respectively. The diaphragm 103 of the incident-side optical system 101 is adapted to direct the light from a light source 105 toward the sample surface S within a predetermined opening angle. The diaphragm 104 of the reflection-side optical system 102 is adapted to direct the reflected light from the sample surface S toward a light receiving surface of a light detector 106 within a predetermined light detection angle. The gloss of the sample surface S is measured, using an output from the light detector 106 which has received the thus-regulated reflected light.

Japanese Unexamined Patent Publication No. Hei 8-29258 discloses an apparatus for measuring the color and the gloss of a sample surface to be measured. The apparatus is provided with a line sensor for receiving light reflected from the sample surface in the direction of the normal, and first and second illumination optical systems disposed at such positions as to illuminate the sample surface with light inclined by 45 degrees with respect to the normal. The one of the illumination optical systems includes a mirror for switching over an optical path between a first position in which the light from a light source provided in the illumination optical system is guided to the sample surface, and a second position in which the light incident to the illumination optical system is reflected to a position different from the position of the light source; and an image sensor for receiving the light reflected from the mirror in the second position. In measuring the color of the sample surface, the first and the second illumination optical systems irradiate the light, with the mirror being set in the first position, and the line sensor receives the light reflected from the sample surface. In measuring the gloss of the sample surface, the first illumination optical system irradiates the light, with the mirror being set in the second position, and the image sensor receives the light reflected from the sample surface.

In use of the reflection characteristic measuring apparatus shown in FIG. 18, as shown in FIG. 19, if the setting position of the sample surface S is tilted by the angle θ, the direction along which the reflected light from the sample surface S is incident onto the reflection-side optical system is tilted by the angle 2θ with respect to the original condition before the tilting. In FIG. 19, the diaphragm 104, the light detector 106, and the like are not illustrated. In this condition, as shown in FIG. 20, assuming that the focal length of a lens element 107 of the reflection-side optical system 102 through which the reflected light is directed toward the light detector 106 is defined as f, the focus position is displaced by f×tan 2θ on the focus plane with respect to the focus position M of reflected light obtained in a condition that the sample surface S is not tilted. In FIG. 20, the solid line shown by the symbol A1 indicates reflected light to be obtained in the case where the sample surface S is not tilted, and the dotted line shown by the symbol A2 indicates reflected light to be obtained in the case where the sample surface S is tilted by the angle θ.

In the conventional measuring apparatus 100, the dimensions of the aperture of the diaphragm 104 provided in the reflection-side optical system 102 are fixed. Accordingly, if the sample surface S is tilted as mentioned above, the amount of reflected light detected by the light detector 106 is varied with respect to a proper condition that the sample surface S is not tilted relative to the measuring apparatus 100. This results in failure of accurate detection of the gloss of the sample surface S.

Also, even if the sum of the amount of reflected light detected by the light detector 106 is identical concerning sample surfaces whose gloss is to be measured, the sample surfaces include sample surfaces having a relatively small ratio of specular reflection light component to diffusion light component as shown in FIG. 21A, and sample surfaces having a relatively large ratio of specular reflection light component to diffusion light component as shown in FIG. 21B. The curves (1) and (2) in FIGS. 21A and 21B show magnitudes of intensities of reflected light with respect to a distance from the reflection point Z. As is obvious from FIGS. 21A and 21B, the intensity of reflected light passing a relevant point on the curve (1), (2) is increased, as the distance from the reflection point Z to the point on the curve (1), (2) is increased.

In the conventional reflection characteristic measuring apparatus 100, the dimensions of the aperture of the diaphragm 104 provided in the reflection-side optical system 102 are fixed, and the gloss of the sample surface is measured based on the sum of light passing through the aperture. Accordingly, if the sum of the amount of reflected light detected by the light detector 106 is identical concerning the sample surfaces to be measured, all the sample surfaces are determined to have the same degree of gloss, which makes it impossible to distinguish the sample surfaces one from the other. Even with use of the apparatus disclosed in the above publication, the drawback cannot be overcome.

SUMMARY OF THE INVENTION

In view of the above problems residing in the conventional examples, it is an object of the present invention to provide a reflection characteristic measuring apparatus that enables to accurately measure a characteristic of a sample surface such as a gloss of the sample surface.

A reflection characteristic measuring apparatus according to an aspect of the invention includes: an illuminator for illuminating a sample surface to be measured with light; a plurality of light receiving sections each adapted for receiving the light reflected on the sample surface illuminated by the light from the illuminator to output two-dimensional light receiving data, respectively; and a deriving section for deriving a characteristic of the sample surface based on a weighted average obtained by applying a weighting factor to each of the light receiving data outputted from the light receiving sections based on an installation condition concerning the illuminator and the light receiving sections, and by averaging the light receiving data weighted with the weighting factors.

A reflection characteristic measuring apparatus according to another aspect of the invention includes: a first optical system having a first illuminator for illuminating a sample surface to be measured with light, a first condenser lens, and a first light receiving sensor, having two-dimensionally arranged pixels, for receiving the light reflected on the sample surface illuminated with the light from the first illuminator; a second optical system having a second illuminator for illuminating the sample surface with light, a second condenser lens, and a second light receiving sensor, having two-dimensionally arranged pixels, for receiving the light reflected on the sample surface illuminated with the light from the second illuminator; and a deriving section for deriving a characteristic of the sample surface, based on an average of first light receiving data outputted from the first light receiving sensor and second light receiving data outputted from the second light receiving sensor, wherein an optical axis of the first optical system and an optical axis of the second optical system are respectively arranged axially symmetrically with respect to a normal of the sample surface set in a proper position at a certain point on a measurement area, and the first optical system and the second optical system are arranged at such positions that the optical axis of the first optical system and the optical axis of the second optical system are at least closely identical to each other to cancel a change of the first light receiving data by a change of the second light receiving data, if a position of the sample surface changes from the proper position.

These and other objects, features and advantages of the present invention will become more apparent upon reading the following detailed description along with the accompanying drawing.

DETAILED DESCRIPTION OF THE PREFERRED EMBODIMENTS

Figure 1:
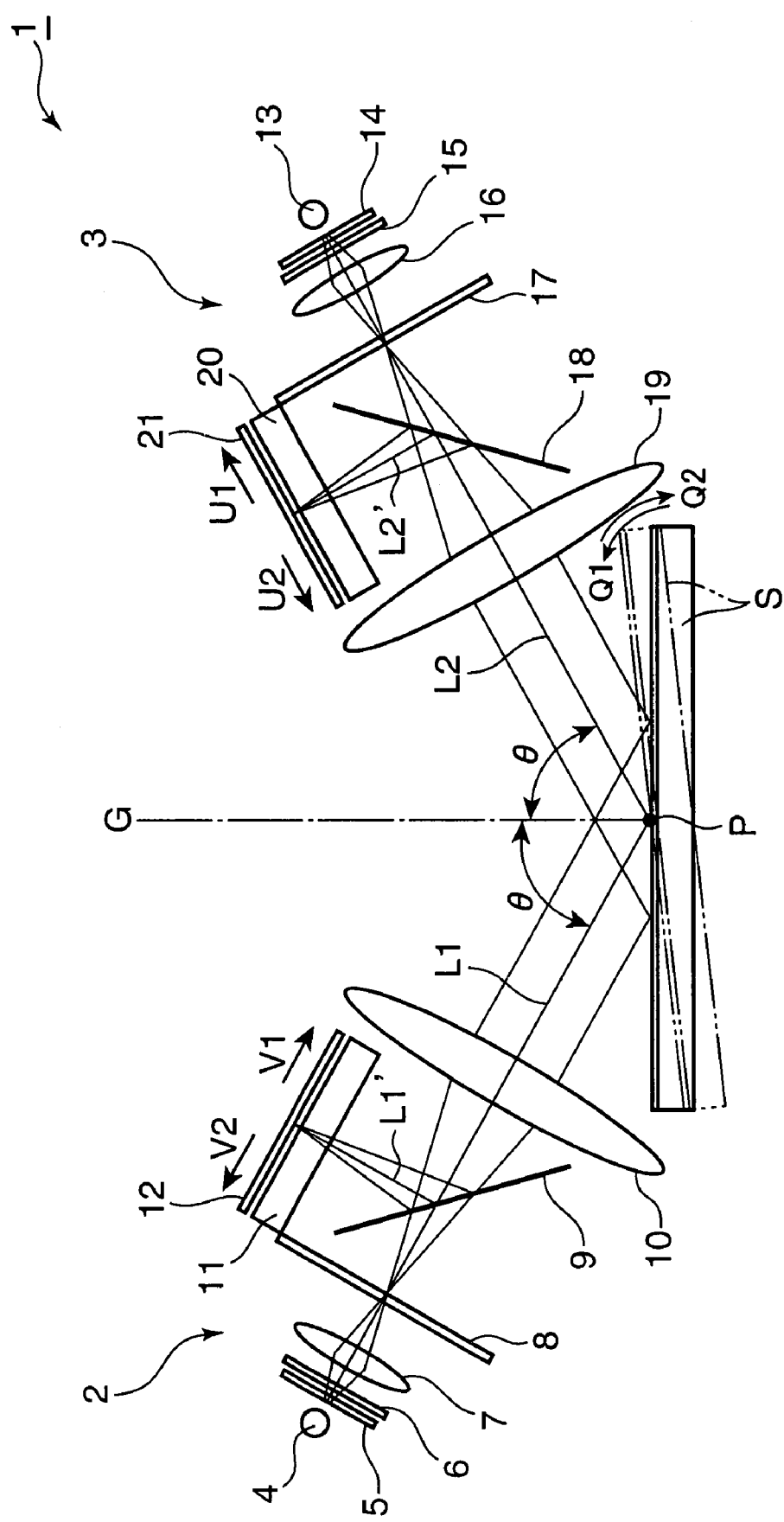
FIG. 1 is a diagram showing a reflection characteristic measuring apparatus embodying the invention.

In the following, a preferred embodiment of a reflection characteristic measuring apparatus according to the invention is described. FIG. 1 is a diagram showing the reflection characteristic measuring apparatus embodying the invention.

As shown in FIG. 1, the reflection characteristic measuring apparatus 1 includes a first light projecting/detecting unit 2 and a second light projecting/detecting unit 3, which are disposed axially symmetrically with each other with respect to a normal G to a sample surface S, when the sample surface S is set in a proper position i.e. a horizontal position in FIG. 1. The first and the second light projecting/detecting units 2 and 3 have substantially identical constructions to each other. The first and the second light projecting/detecting units 2 and 3 output light toward the intersection P at such positions that optical axes L1 and L2 thereof define an angle θ (θ is e.g. 60°, hereinafter, the angle θ is called as "incident angle θ") with respect to the normal G when the sample surface S is set in the proper position. The incident angle θ is defined by ISO2813, ISO7668, JIS Z8741 or a like criterion, and may be e.g. 20° or 80°.

Throughout the specification, the expression "setting position of the sample surface is not changed" means that the sample surface is not tilted i.e. the sample surface is set in a proper position, and the expression "setting position of the sample surface is changed" means that the sample surface is tilted with respect to the proper position.

The first light projecting/detecting unit 2 includes, on the optical axis L1, a light source 4 as a first illuminator, a light diffusing plate 5, a restraining plate 6, a first lens element 7 as a first condenser lens, a diaphragm 8, a half mirror 9, and a second lens element 10 in this order from the farthest position from the intersection P. A filter section 11 and an image sensor 12 as a second light receiving sensor are arranged at their respective predetermined positions in the first light projecting/detecting unit 2.

The light source 4 includes e.g. an LED (Light Emitting Diode), and outputs light toward the intersection P on the sample surface S to be measured. The light diffusing plate 5 diffuses the light outputted from the light source 4. The restraining plate 6 is a plate-like member formed with a slit for defining an illumination area. The first lens element 7 condenses the light transmitted through the restraining plate 6. The diaphragm 8 controls the light transmitted through the first lens element 7 to be incident within a certain angle corresponding to a rectangular area, and is disposed on a focus position of the second lens element 10 in the direction of the optical axis L1.

The half mirror 9 is arranged with an inclination of e.g. 45° with respect to the optical axis L1. The half mirror 9 transmits the light transmitted through the diaphragm 8 toward the second lens element 10, and reflects the light from the second lens element 10 along an optical axis inclined by e.g. 90° with respect to the optical axis L1. The second lens element 10 guides the light transmitted through the half mirror 9 as substantially parallel light toward the sample surface S.

The filter section 11 includes an infrared blocking filter for reducing an infrared component included in the light (hereinafter, called as "reflected light") reflected by the half mirror 9, and an LPF (low-pass filter) for blocking a high frequency component of the reflected light.

The image sensor 12 is a CCD (Charge Coupled Device) area sensor provided with a substantially rectangular light receiving surface, on which multitudes of photoelectric conversion elements (hereinafter, called as "pixels") constituted of e.g. photodiodes are two-dimensionally arranged in a matrix. The image sensor 12 is arranged at a position equivalent to the focus position of the second lens element 10, and is set at a position substantially orthogonal to an optical axis L1' of light reflected by the half mirror 9 at a substantially center of the light receiving surface thereof, in the case where the sample surface S is set in the proper position and the light reflected on the sample surface S is parallel light. The image sensor 12 converts a subject light image formed on the light receiving surface of the image sensor 12 via the filter section 11 into analog electric signals for output as pixel signals. The image sensor 12 may include a CMOS image sensor, other than the CCD area sensor.

The second light projecting/detecting unit 3 has substantially the same arrangement as the first light projecting/detecting unit 2. The second light projecting/detecting unit 3 includes, on the optical axis L2, a light source 13 as a second illuminator, a light diffusing plate 14, a restraining plate 15, a first lens element 16 as a second condenser lens, a diaphragm 17, a half mirror 18, and a second lens element 19 in this order from the farthest position from the intersection P. A filter section 20 and an image sensor 21 are arranged at their respective predetermined positions in the second light projecting/detecting unit 3.

The light source 13 has substantially the same arrangement as the light source 4 in the first light projecting/detecting unit 2, and outputs light toward the intersection P on the sample surface S. The light diffusing plate 14 diffuses the light outputted from the light source 13. The restraining plate 15 is a plate-like member formed with a slit for defining an illumination area. The first lens element 16 condenses the light transmitted through the restraining plate 15. The diaphragm 17 controls the light transmitted through the first lens element 16 to be incident within a certain angle, and is disposed on a focus position of the second lens element 19 in the direction of the optical axis L2.

The half mirror 18 is arranged with an inclination of e.g. 45° with respect to the optical axis L2. The half mirror 18 transmits the light transmitted through the diaphragm 17 toward the second lens element 19, and reflects the light from the second lens element 19 along an optical axis inclined by e.g. 90° with respect to the optical axis L2. The second lens element 19 guides the light transmitted through the half mirror 18 as substantially parallel light toward the sample surface S.

Figure 2:
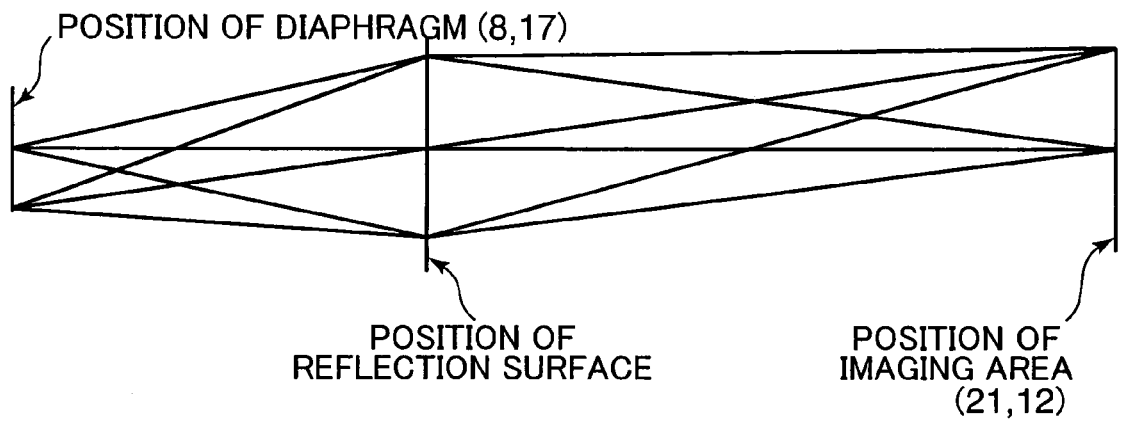
FIG. 2 is a diagram showing behaviors of light directed from a second lens element toward a sample surface to be measured, and of light directed toward an image sensor.

The filter section 20 and the image sensor 21 have substantially the same arrangements as the filter section 11 and the image sensor 12, respectively. The image sensor 21 is arranged at a position equivalent to the focus position of the second lens element 19, and is set at a position substantially orthogonal to an optical axis L2' of light reflected by the half mirror 18 at a substantially center of the light receiving surface thereof, in the case where the sample surface S is set in the proper position and the light reflected on the sample surface S is parallel light. As shown in FIG. 2, the light receiving surface of the image sensor 21 and the diaphragm 8 are positioned in optically conjugated relations with each other, and the light receiving surface of the image sensor 12 and the diaphragm 17 are positioned optically conjugated relations with each other, respectively.

The image sensor 12, 21 has a longer side of the light receiving surface thereof extending in a direction orthogonal to the plane of FIG. 1. The light to be guided to the light receiving surface of the image sensor 12, 21 i.e. the light reflected by the half mirror 9, 18 has a rectangular shape in cross section, taken along a plane orthogonal to the optical axis L1' L2'. The longer side of the cross section of the light is substantially parallel to the longer side of the light receiving surface of the image sensor 12, 21, and the shorter side thereof is substantially parallel to the shorter side of the light receiving surface of the image sensor 12, 21.

When the light outputted from the light source 4 has reached the sample surface S via the optical components 5 through 10 of the first light projecting/detecting unit 2, the light is reflected by the sample surface S. The reflected light is transmitted through the second lens element 19, reflected on the half mirror 18, and then is received by the image sensor 21 via the filter section 20 in the second light projecting/detecting unit 3.

When the light outputted from the light source 13 has reached the sample surface S via the optical components 14 through 19 of the second light projecting/detecting unit 3, the light is reflected on the sample surface S. The reflected light is transmitted through the second lens element 10, reflected by the half mirror 9, and then is received by the image sensor 12 via the filter section 11 in the first light projecting/detecting unit 2.

Observing optical paths of light projection/detection in the reflection characteristic measuring apparatus of the embodiment, the reflection characteristic measuring apparatus includes two optical systems i.e. first and second optical systems. The first optical system defines an optical path from the light source 4 of the first light projecting/detecting unit 2 to the image sensor 21 of the second light projecting/detecting unit 3. Specifically, the first optical system is constituted of the light diffusing plate 5, the restraining plate 6, the first lens element 7, the diaphragm 8, and the second lens element 10 of the first light projecting/detecting unit 2, and the second lens element 19 and the half mirror 18 of the second light projecting/detecting unit 3. On the other hand, the second optical system defines an optical path from the light source 13 of the second light projecting/detecting unit 3 to the image sensor 12 of the first light projecting/detecting unit 2. Specifically, the second optical system is constituted of the light diffusing plate 14, the restraining plate 15, the first lens element 16, the diaphragm 17, and the second lens element 19 of the second light projecting/detecting unit 3, and the second lens element 10 and the half mirror 9 of the first light projecting/detecting unit 2. Thus, the first and the second optical systems share the optical components, and the optical axes of the first and the second optical systems are at least closely identical to each other. More specifically, the optical axes of the first and the second optical systems are identical to each other between the half mirrors 9 and 18.

The light reflected on the sample surface S includes a specular reflection light component whose angle (hereinafter, called as "reflected angle") with respect to the normal G is substantially the same or close to the incident angle θ, and a diffusion light component. Whereas a sample surface with more gloss has a larger ratio of specular reflection light component to diffusion light component, in other words, a smaller ratio of diffusion light component to specular reflection light component, a sample surface with less gloss has a larger ratio of diffusion light component, in other words, a smaller ratio of specular reflection light component. The reflection characteristic measuring apparatus 1 measures the gloss of the sample surface S i.e. the degree of reflection in the case where the sample surface is illuminated with light, based on the amount of reflected light composed of the specular reflection light component and the diffusion light component.

Figure 3:
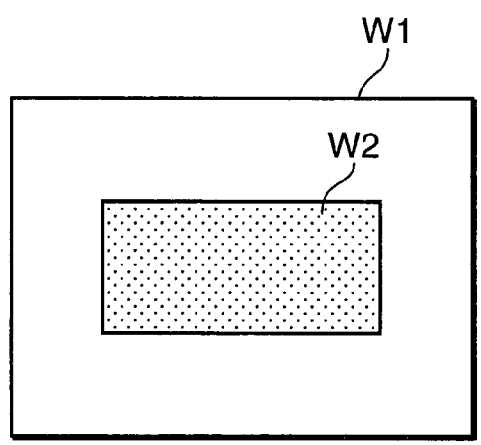
FIG. 3 is a diagram showing a relationship between a light receiving area W1 of the image sensor, and an area W2 within which light reflected from the sample surface is irradiated onto a light receiving surface of the image sensor.

FIG. 3 is a diagram showing a relation between a light receiving area W1 of the image sensor 12, 21, and a targeted area W2 where the gloss of the sample surface S is to be measured. In the embodiment, the targeted area W2 for gloss measurement has dimensions corresponding to the aperture of the diaphragm 104 of the conventional reflection characteristic measuring apparatus 100. As shown in FIG. 3, the image sensor 12, 21 has the light receiving area W1 larger than the targeted area W2 for gloss measurement i.e. W1>W2.

In use of the reflection characteristic measuring apparatus 1 having the above arrangement, in the case where the sample surface S is set to a tilted position where the sample surface S is angularly displaced counterclockwise about the intersection P i.e. in the direction shown by the arrow Q1 in FIG. 1, a light image i.e. a peak position on the light receiving surface of the image sensor 21 is displaced in the direction of the arrow U1 with respect to a light image i.e. a peak position to be obtained when the sample surface S is set in the proper position. Likewise, a light image i.e. a peak position on the light receiving surface of the image sensor 12 is displaced in the direction of the arrow V1 with respect to the light image i.e. the peak position to be obtained when the sample surface S is set in the proper position.

On the other hand, in the case where the sample surface S is set to a tilted position where the sample surface S is angularly displaced clockwise about the intersection P i.e. in the direction shown by the arrow Q2 in FIG. 1, a light image i.e. a peak position on the light receiving surface of the image sensor 21 is displaced in the direction of the arrow U2 with respect to the light image i.e. the peak position to be obtained when the sample surface S is set in the proper position. Likewise, a light image i.e. a peak position on the light receiving surface of the image sensor 12 is displaced in the direction of the arrow V2 with respect to the light image i.e. the peak position to be obtained when the sample surface S is set in the proper position.

As far as the sample surface S is set in an allowable tilt angle range, the focal length of the second lens element 19 of the second light projecting/detecting unit 3 is set in such a manner that the light image i.e. the peak position derived from the light source 4 of the first light projecting/detecting unit 2 is located on the light receiving surface of the image sensor 21, and the focal length of the second lens element 10 of the first light projecting/detecting unit 2 is set in such a manner that the light image i.e. the peak position derived from the light source 13 of the second light projecting/detecting unit 3 is located on the light receiving surface of the image sensor 12, respectively.

Figure 4:
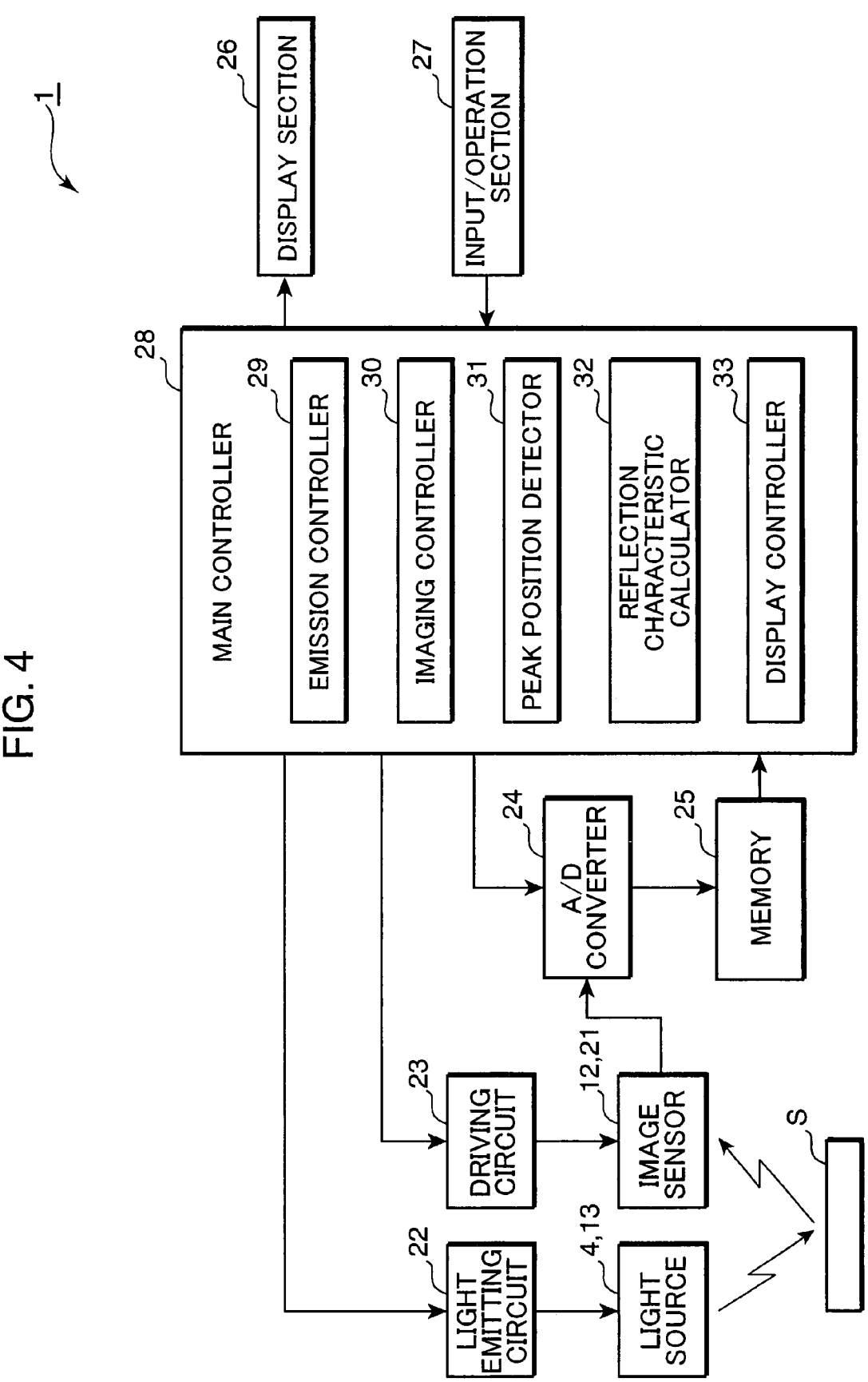
FIG. 4 is a block diagram showing an electrical configuration of the reflection characteristic measuring apparatus.

FIG. 4 is a block diagram showing an electrical configuration of the reflection characteristic measuring apparatus 1. As shown in FIG. 4, the reflection characteristic measuring apparatus 1 includes light sources 4, 13, image sensors 12, 21, a light emitting circuit 22, a driving circuit 23, an A/D converter 24, a memory 25, a display section 26, an input/operation section 27, and a main controller 28.

The light sources 4, 13, and the image sensors 12, 21 in FIG. 4 correspond to the light sources 4, 13, and the image sensors 12, 21 shown in FIG. 1, respectively. The light emitting circuit 22 causes the light source 4, 13 to emit light in accordance with a command signal from the main controller 28. The driving circuit 23 causes the image sensor 12, 21 to perform an imaging operation in accordance with a command signal from the main controller 28.

The A/D converter 24 converts pixel signals outputted from the image sensor 12, 21 into digital pixel signals (hereinafter, called as "pixel data") constituted of plural bits e.g. 10 bits. The memory 25 temporarily stores the pixel data outputted from the A/D converter 24, and is used as a working area in which the main controller 28 implements various processing with respect to the pixel data.

The display section 26 includes e.g. an LCD (Liquid Crystal Display), and displays the degree of gloss of the sample surface S obtained by the main controller 28. The input/operation section 27 includes a power button for allowing a user to turn on and off a main power supply of the reflection characteristic measuring apparatus 1, and switches for allowing the user to enter designation to start gloss measurement concerning the sample surface S.

The main controller 28 includes a microcomputer built-in with a storage such as an ROM (Read Only Memory) in which e.g. a control program or the like is stored, or a flash memory for temporarily storing data.

Figure 5:
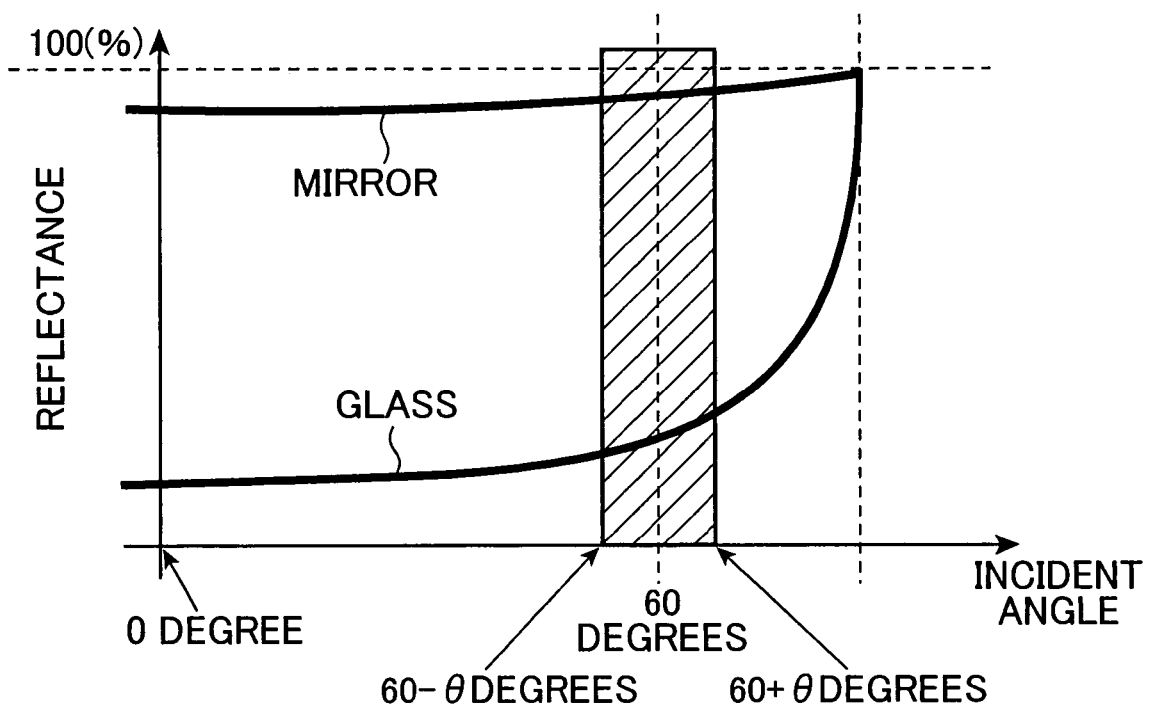
FIG. 5 is a graph showing relations between an incident angle and a reflectance of specular reflection light corresponding to an amount of specular reflection light in the case where the sample surface is a mirror surface and the sample surface is a glass surface.

The specular reflection light component has a characteristic that it is likely to be absorbed by the sample surface S, as the incident angle θ is close to 0°. Accordingly, the intensity i.e. the light amount of the specular reflection light component is increased, as the incident angle is increased. FIG. 5 is a graph showing relations between an incident angle, and a reflectance of a specular reflection light component corresponding to a light amount of the specular reflection light component in the case where the sample surface S is a mirror surface, and the sample surface S is a glass surface. In FIG. 5, the axis of abscissas indicates the incident angle, and the axis of ordinate indicates the reflectance of the specular reflection light component, respectively. As shown in FIG. 5, both in the cases where the sample surface is a mirror surface, and the sample surface is a glass surface, the reflectance of the specular reflection light component is increased, as the incident angle is increased. In the case where the sample surface is a glass surface, the reflectance of the specular reflection light component is sharply increased when the incident angle exceeds a predetermined value.

On the other hand, the diffusion light component has a characteristic that the intensity i.e. the light amount thereof is decreased, as the incident angle is increased. Assuming that the light is outputted from the light source 4, 13 with the incident angle θ, and the reflection light from the sample surface S is received by the image sensor 12, 21 with the light receiving amount d(θ) at a position inclined by the angle θ with respect to the normal G in the area opposite to the light source 4, 13 with respect to the normal G, it is known that the light receiving amount d(θ) is expressed by k×cos θ where k is a constant.

The above leads to a conclusion that the intensity of the specular reflection light component and the intensity of the diffusion light component are different between a condition that the sample surface S is set in a proper position, and a condition that the sample surface S is set in a tilted position, because the incident angle is different between the condition that the sample surface S is set in the proper position, and the condition that the sample surface S is set in the tilted position. As a result, a measurement error is generated concerning the ratio of the specular reflection light component to the diffusion light component in the condition that the sample surface S is set in the tilted position, as compared with the condition that the sample surface S is set in the proper position.

In view of the above, in the embodiment, as mentioned above, the light sources 4 and 13 are arranged axially symmetrically with each other with respect to the normal G, and the image sensors 12 and 21 are disposed at the optically equivalent positions, respectively. The gloss of the sample surface S is measured by implementing a process of eliminating or reducing a measurement error resulting from a difference in the ratio of the specular reflection light component to the diffusion light component between the condition that the sample surface S is set in the tilted position, and the condition that the sample surface S is set in the proper position, which will be described below, using the light receiving data i.e. first light receiving data obtained from the image sensor 12 and the light receiving data i.e. second light receiving data obtained from the image sensor 21.

As shown in FIG. 4, the main controller 28 functionally has an emission controller 29, an imaging controller 30, a peak position detector 31, a reflection characteristic calculator 32, and a display controller 33.

The emission controller 29 controls an operation of the light emitting circuit 22. Upon receiving a designation to start gloss measurement concerning the sample surface S by way of the input/operation section 27, the emission controller 29 controls the light sources 4 and 13 to alternately emit light for a predetermined time duration.

The imaging controller 30 controls an operation of the driving circuit 23. Upon receiving a designation to start gloss measurement concerning the sample surface S by way of the input/operation section 27, the imaging controller 30 controls the image sensor 12, 21 to perform an imaging operation while the light is alternately emitted from the light sources 4 and 13. Specifically, the imaging controller 30 controls the image sensor 21 to perform an imaging operation when the emission controller 29 controls the light source 4 to emit light, and controls the image sensor 12 to perform an imaging operation when the emission controller 29 controls the light source 13 emit light.

Figure 6:
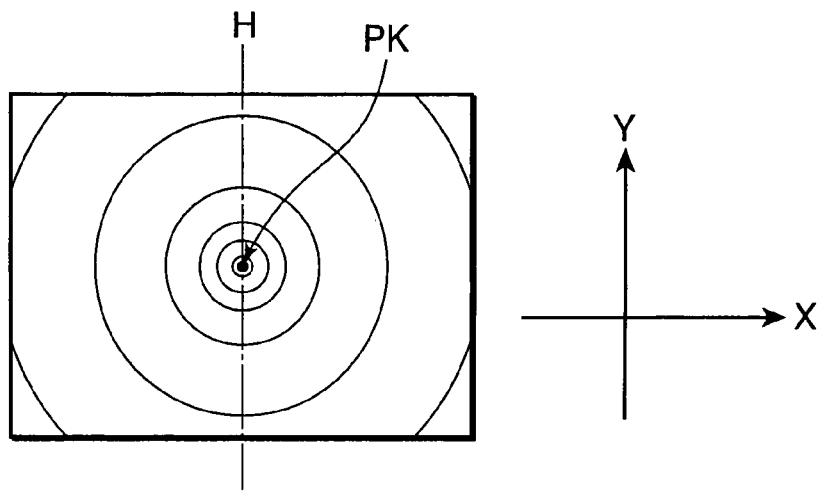
FIG. 6 is a diagram showing an intensity distribution of reflected light including a peak value in the case where the setting position of the sample surface is not changed.

The peak position detector 31 detects a targeted pixel (hereinafter, the position of the targeted pixel is called as "peak position") which outputs a maximal output value among output values of the pixels of the image sensor 12, 21. As mentioned above, a sample surface with more gloss has a larger ratio of specular reflection light component to diffusion light component. Concerning a sample surface S with a relatively large degree of gloss, there is a pixel having a relatively large output value (hereinafter, called as "peak value"), as compared with the output values of the other pixels. The peak value is generated primarily because of the specular reflection light component. FIG. 6 is a diagram showing an intensity distribution on reflected light having the peak value in the case where the setting position of the sample surface S is not changed.

As shown in FIG. 6, in the case where the light reflected on the sample surface S has the peak value, the peak value appears at a certain position i.e. the peak position PK where the output value is significantly increased. Also, the output value of the pixel is decreased, as the distance from the peak position PK is increased. By connecting the pixels having substantially the same output values by a line, an output distribution profile is obtained, in which substantially concentric circles are depicted, with the peak position PK serving as a center of the circles.

On the other hand, concerning a sample surface S with a relatively small degree of gloss, the light received on the image sensor 12, 21 includes a relatively large ratio of diffusion light component. Accordingly, in this case, the intensity distribution concerning the reflected light on the light receiving surface of the image sensor 12, 21 shows a moderate gradient, and the output values of the pixels of the image sensor 12, 21 do not include the aforementioned peak value.

The peak position detector 31 detects whether the output distribution profile concerning the pixels includes the peak value with respect to the light receiving data acquired by the imaging operation by the image sensor 12, 21. If it is detected that the output distribution profile includes the peak value, the peak position detector 31 judges the pixel which has outputted the peak value, as a pixel which has received the specular reflection light, and defines the position of the pixel as the peak position. If, on the other hand, it is detected that the output distribution profile does not include the peak value, the peak position detector 31 judges that the peak position does not exist concerning the light receiving data.

The following is an example of the method for detecting whether the output distribution profile includes the peak value. First, pixel output values are compared one with the other to detect a maximal output value, and the output value of a pixel adjacent the pixel having the maximal output value is extracted. Then, if a difference between the extracted output value and the maximal output value is equal to or larger than a predetermined value, it is judged that the light receiving data includes a peak value, and if the difference is smaller than the predetermined value, it is judged that the light receiving data does not include a peak value.

The reflection characteristic calculator 32 calculates the degree of gloss of the sample surface S, using the following approach. First, the reflection characteristic calculator 32 defines a predetermined area having predetermined dimensions including the peak position as a reference position, as a trimming area, if the peak position detector 31 judges that the light receiving data includes a peak value.

Figure 7:
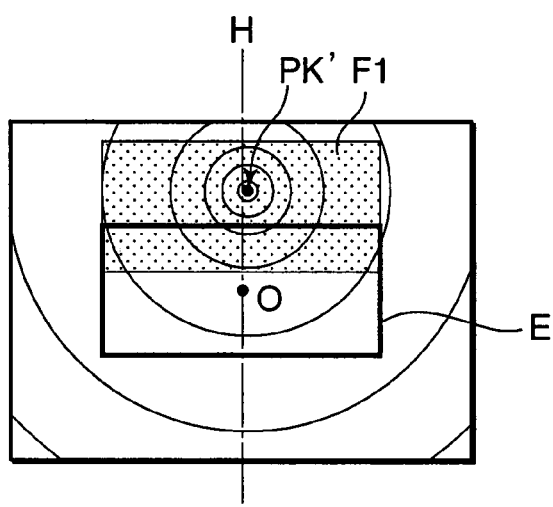
FIG. 7 is a diagram showing an intensity distribution of reflected light in the case light receiving data obtained from one of the image sensors includes a peak value when the setting position of the sample surface is changed.

For instance, assuming that the peak position of the light receiving data obtained from the image sensor 21 is displaced from the peak position PK shown in FIG. 6 to the peak position PK' shown in FIG. 7 resulting from a change of the setting position of the sample surface S, then, the reflection characteristic calculator 32 defines a predetermined area F1 including the peak position PK' as a center thereof, as a trimming area.

Figure 8:
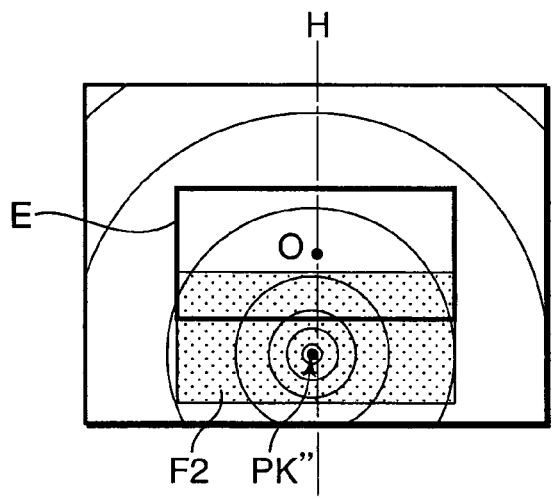
FIG. 8 is a diagram showing an intensity distribution of reflected light in the case light receiving data obtained from the other of the image sensors includes a peak value when the setting position of the sample surface is changed.

Likewise, assuming that the peak position of the light receiving data obtained from the image sensor 12 is displaced from the peak position PK shown in FIG. 6 to the peak position PK" shown in FIG. 8 resulting from a change of the setting position of the sample surface S, then, the reflection characteristic calculator 32 defines a predetermined area F2 including the peak position PK" as a center thereof, as a trimming area. The predetermined area F1, F2 has dimensions substantially identical to the dimensions of the targeted area W2 (see FIG. 3).

Figure 9:
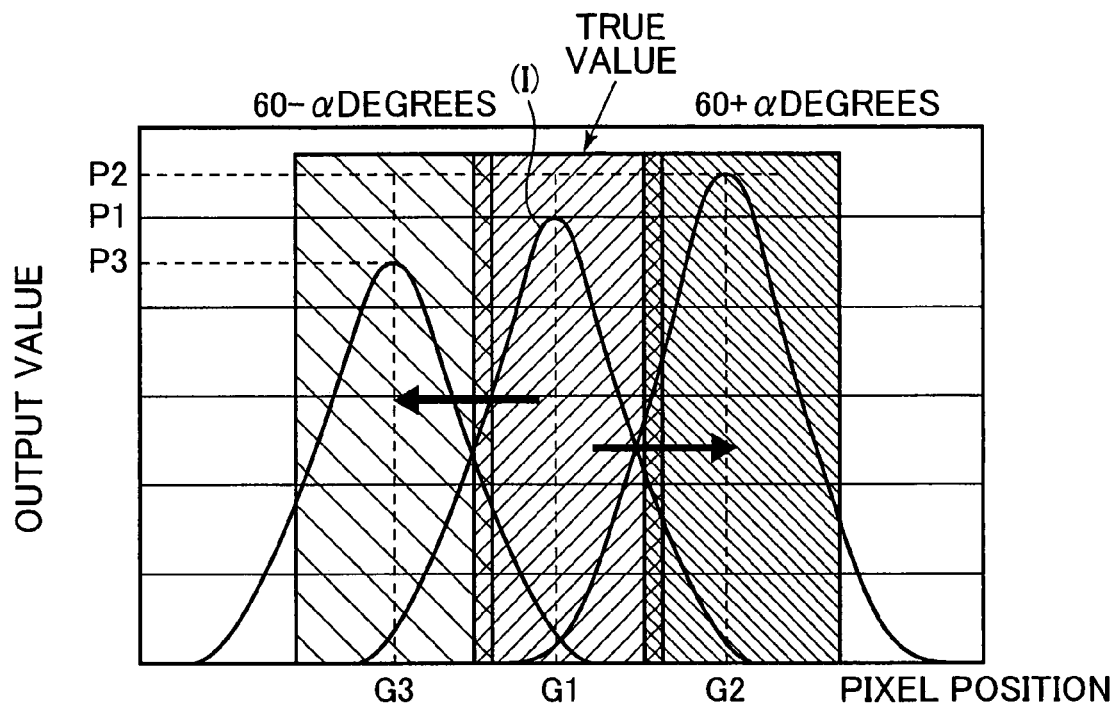
FIG. 9 is a graph showing light amount distributions, concerning the light receiving data including the peak value, at pixel positions on an imaginary line segment H in FIG. 6, wherein the line segment H passes a peak position PK in FIG. 6 and extends parallel to a shorter side direction of the respective image sensors when the sample surface is set in a proper position.

FIG. 9 is a graph showing light amount distributions, concerning the light receiving data including the pixel value, at pixel positions on an imaginary line segment H in FIG. 6, wherein the line segment H passes the peak position PK (see FIG. 6), and extends parallel to the shorter side direction of the image sensor 12, 21 when the sample surface S is set in the proper position. In FIG. 9, the axis of abscissas indicates the pixel position, and the axis of ordinate indicates the light receiving amount on the respective pixel positions.

As shown in FIG. 9, in the case where the sample surface S is set in the proper position, let it be assumed that the pixel which has outputted a peak value P1 among the light receiving data obtained by the imaging operation by the image sensor 12, 21 is indicated as a pixel G1. Then, the light receiving data obtained by the imaging operation by the image sensor 12, 21 has a distribution profile shown by the waveform (I), in which the pixel G1 has the peak value P1.

In the above condition, let it be assumed that the setting position of the sample surface S is angularly displaced counterclockwise about the intersection P i.e. in the direction shown by the arrow Q1 in FIG. 1. In this condition, the peak position of the light received on the image sensor 21 is displaced from e.g. the peak position PK shown in FIG. 6 to the peak position PK' shown in FIG. 7 i.e. PK→PK' in one of the shorter side directions of the image sensor 21 i.e. in the upward direction. As a result, as shown in FIG. 9, the pixel which is supposed to output the peak value is shifted from the pixel G1 to a pixel G2. Also, the incident angle to the sample surface S is increased, as the setting position of the sample surface S is changed from the proper position to the tilted position. Accordingly, the peak value of the light received on the image sensor 21 is shifted to a peak value P2, which is larger than the peak value P1.

On the other hand, in the case where the peak position of the light received on the image sensor 12 is angularly displaced from e.g. the peak position PK shown in FIG. 6 to the peak position PK" shown in FIG. 8 i.e. PK→PK" in the other of the shorter side directions of the image sensor 12 i.e. in the downward direction, as shown in FIG. 9, the pixel which is supposed to output the peak value is shifted from the pixel G1 to a pixel G3. Further, the incident angle to the sample surface S is decreased, as the setting position of the sample surface S is changed from the proper position to the tilted position. Accordingly, the peak value of the light received on the image sensor 12 is shifted to a peak value P3, which is smaller than the peak value P1.

As shown in FIG. 5, by setting the incident angle to about 60° when the sample surface S is set in the proper position, the reflectance of the specular reflection light is monotonously changed both in the cases that the sample surface S is a mirror surface and a glass surface, as far as the setting position of the sample surface S lies in a predetermined range, in other words, the variation of the incident angle θ lies in a range indicated by the hatched portion in FIG. 5. In other words, as shown by the straight line A in FIG. 10, it is conceived that the incident angle θ and the reflectance i.e. the intensity of the specular reflection light component has a proportional relation. The straight line A shown in FIG. 10 is a graph showing a change of the reflectance when the incident angle θ is in a range near 60°.

Figure 10:
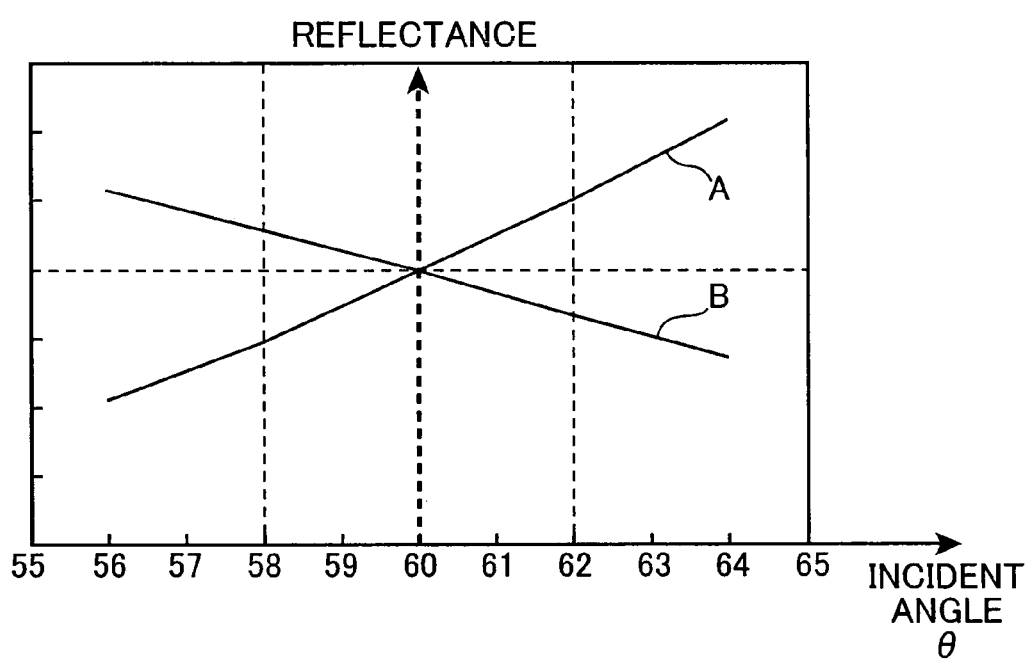
FIG. 10 is a graph showing relations between an incident angle and a reflectance concerning a specular reflection light component and a diffusion light component.

The straight line B shown in FIG. 10 is a graph showing a change of the diffusion light component when the incident angle θ is in the range near 60°. As shown in FIG. 10, when the incident angle θ is in the range near 60°, the reflectance of the diffusion light component i.e. the intensity of the diffusion light component is monotonously changed, and the diffusion light component is decreased substantially proportional to the incident angle.

A variation (absolute value) of the reflectance with respect to the incident angle of the light incident onto the image sensor 21 is substantially identical to a variation (absolute value) of the reflectance with respect to the incident angle of the light incident onto the image sensor 12 concerning both of the specular reflection light component and the diffusion light component. Accordingly, assuming that the average of the output values of the pixels belonging to a predetermined area F including the peak position PK as a center when the sample surface S is in the proper position is represented by P4, it is conceived that |P4−P5| is substantially equal to |P6−P4| where |P4−P5| is a decreased rate (absolute value) from an average P4 to an average P5, and |P6−P4| is an increased rate (absolute value) from the average P4 to an average P6.

Specifically, by averaging the light receiving data obtained from the image sensors 12, 21 with respect to the predetermined area F concerning the specular reflection light component and the diffusion light component, an increment i.e. a difference in increase of the light receiving data obtained from one of the image sensors 12 and 21, and a decrement i.e. a difference in decrease of the light receiving data obtained from the other of the image sensors 12 and 21 are cancelled. Thus, it is conceived that a mean value of the averages P5 and P6 i.e. (P5+P6)/2 is approximated to the average P4 to be obtained when the sample surface S is set in the proper position.

The reflection characteristic calculator 32 sets weighting factors to be multiplied by the average P5 and the average P6 to one, respectively. Then, the reflection characteristic calculator 32 calculates an average of multiplications obtained by respectively multiplying the average P5 and the average P6 by the weighing factors i.e. implements the expression: (1×P5+1×P6)/2, and calculates the gloss of the sample surface S, using a predetermined computation formula based on the mean value i.e. (P5+P6)/2.

The weighting factor is a value to be determined depending on an installation condition including the installation sites and the number of the light sources 4 and 13, and the image sensors 12 and 21. In this embodiment, the light sources 4 and 13 are provided in correspondence to the image sensors 12 and 21. Since the light source 4 and the light source 13, and the image sensor 12 and the image sensor 21 are disposed axially symmetrically with each other with respect to the normal G, respectively, the weighting factors for the light receiving data obtained from the image sensors 12 and 21 are identical to each other. In other words, the optical axes of the first and the second optical systems are arranged symmetrically with each other with respect to the normal G, and the optical axes of the first and the second optical systems are at least closely identical to each other. Accordingly, the gloss of the sample surface S can be obtained substantially merely by performing simple averaging with respect to the light receiving data obtained from the image sensors 12 and 21.

On the other hand, in the case where the peak position detector 31 judges that there does not exist a peak value, the reflection characteristic calculator 32 defines a predetermined area having predetermined dimensions including the center position O of the light receiving surface of the image sensor 12, 21 as a reference position, as a trimming area. The reflection characteristic calculator 32 calculates the sum of the output values of the pixels belonging to each of the trimming areas, and calculates the gloss of the sample surface S, using the aforementioned computation formula, based on the average value of the sums.

The display controller 33 controls the display section 26 to display the gloss calculated by the reflection characteristic calculator 32.

Figure 11:
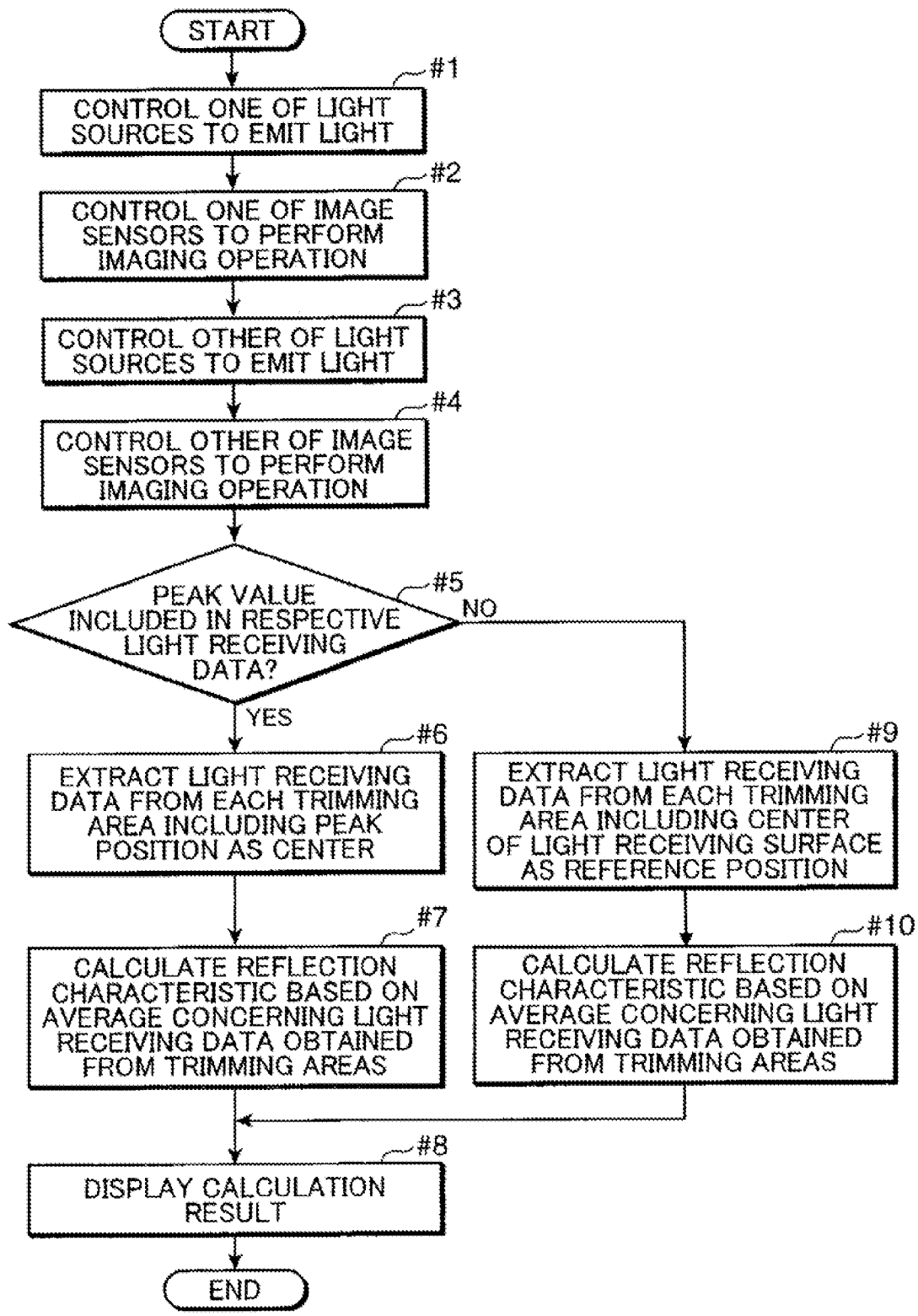
FIG. 11 is a flowchart showing a gloss measurement operation to be executed by the reflection characteristic measuring apparatus.

In the following, a gloss measurement operation to be executed by the reflection characteristic measuring apparatus 1 having the above arrangement is described referring to a flowchart shown in FIG. 11. When the process enters a routine shown in FIG. 11, the main controller 28 controls the light source 4 to emit light (Step #1), and controls the image sensor 21 to perform an imaging operation (Step #2). Then, the main controller 28 controls the light source 13 to emit light (Step #3), and controls the image sensor 12 to perform an imaging operation (Step #4).

Then, the main controller 28 controls the peak position detector 31 to detect whether the light receiving data obtained from the image sensor 12, 21 includes a peak value (Step #5). If it is detected that the light receiving data obtained from the image sensor 12, 21 includes the peak value (YES in Step #5), the light receiving data corresponding to a predetermined area e.g. the trimming area F1, F2 including the pixel corresponding to the peak position at which the peak value has been outputted as a center is extracted as a trimming area (Step #6). Then, a reflection characteristic i.e. a degree of gloss of the sample surface S is calculated, using the predetermined computation formula, based on the average value of the light receiving data obtained with respect to the trimming areas (Step #7). Then, the main controller 28 controls the display controller 33 to display the calculated reflection characteristic on the display section 26 (Step #8).

If, on the other hand, the peak position detector 31 detects that the light receiving data does not include a peak value in Step #5 (NO in Step #5), the controller 28 is operative to extract light receiving data corresponding to a predetermined area including the center position O of the light receiving surface of the image sensor 12, 21 as a reference position, as a trimming area (Step #9). Then, a reflection characteristic i.e. a degree of gloss of the sample surface S is calculated, using the predetermined computation formula, based on the average value of the light receiving data obtained with respect to the trimming areas (Step #10). Then, the main controller 28 controls the display controller 33 to display the calculated reflection characteristic on the display section 26 (Step #8).

As mentioned above, in the embodiment, the light sources 4 and 13 are disposed axially symmetrically with each other with respect to the normal G to the sample surface S in the proper position at the certain point P on a measurement area. The image sensors 12 and 21 for receiving the light reflected on the sample surface S illuminated with the light outputted from the light sources 4 and 13 are arranged at the respective predetermined positions. A reflection characteristic i.e. a degree of gloss of the sample surface S is measured, using the light receiving data obtained from the image sensors 12 and 21 when the light sources 4 and 13 are alternately caused to emit light. This enables to accurately measure the gloss, as compared with an arrangement that a single light source and a single image sensor are provided.

In the arrangement of the embodiment, in the case where it is judged that the light receiving data obtained from each of the image sensors 12 and 21 includes a peak value, the light receiving data corresponding to the predetermined area including the peak position at which the peak value has been outputted as the center are extracted as the trimming areas, and the reflection characteristic i.e. the degree of gloss of the sample surface S is computed, using the predetermined computation formula based on the average value of the light receiving data concerning the trimming areas. This enables to eliminate or reduce a measurement error concerning the specular reflection light component and the diffusion light component resulting from a change in the setting position of the sample surface S, even if the sample surface to be measured has a high degree of gloss.

In the case where it is judged that the light receiving data does not include a peak value, the predetermined area having the pixel at the center position O of the light receiving surface of each of the image sensors 12 and 21 as a reference pixel, is defined as the trimming area. The gloss of the sample surface S is measured based on the output values from the pixels belonging to the trimming areas. This enables to accurately measure the characteristic of the sample surface S by suppressing a measurement error resulting from a change in the setting position of the sample surface S, even if the peak value is not detected.

The invention may include the following modifications (1) through (4) in addition to or in place of the foregoing embodiment.

(1) In the foregoing embodiment, the method for detecting the maximal output value i.e. the peak value among the pixel output values to define the position of the pixel which has outputted the peak value as the peak position is adopted as the method for detecting the peak position. Alternatively, the following method may be applied to detect the peak position.

Figure 12:
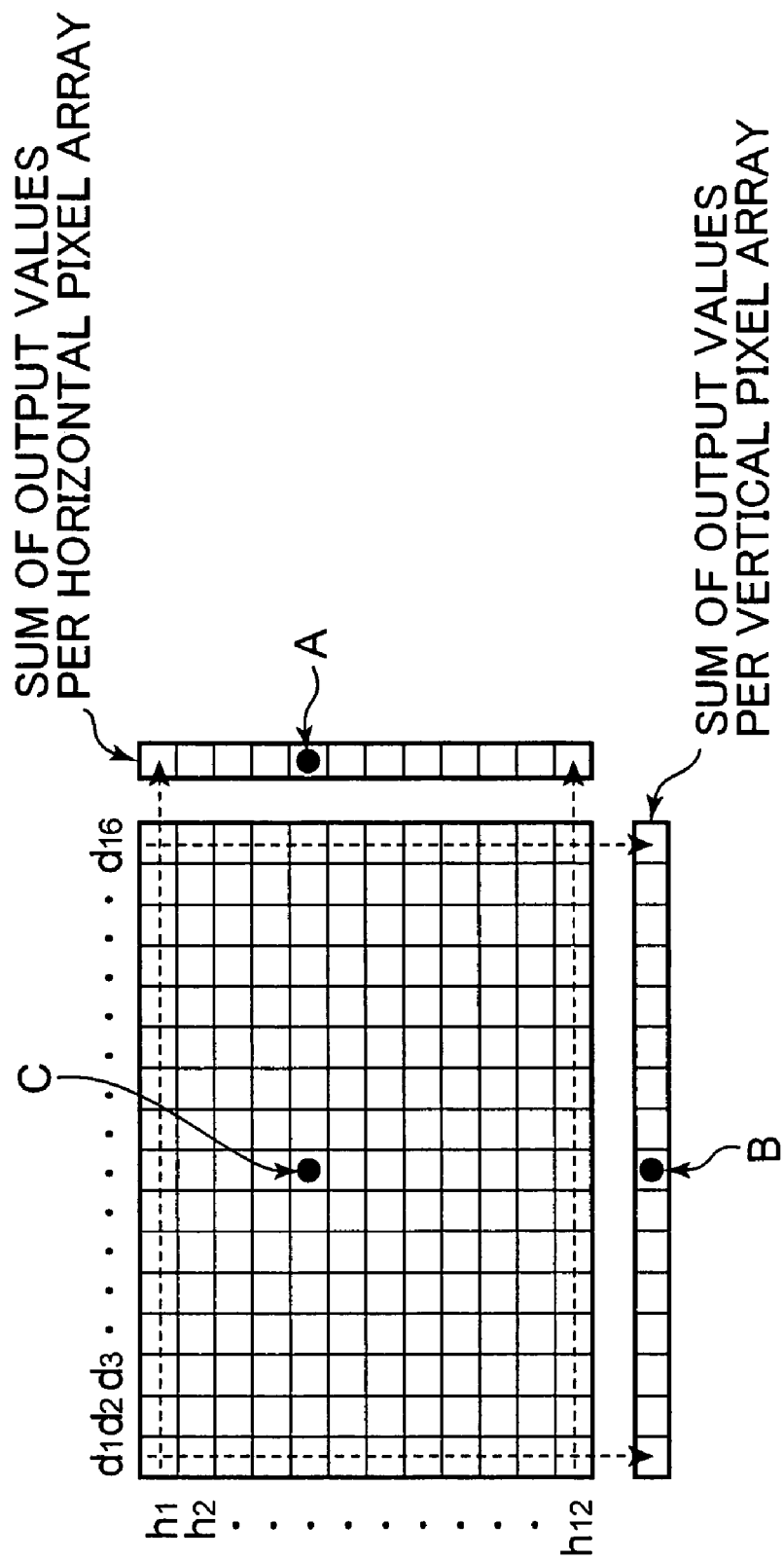
FIG. 12 is a diagram for describing another approach for detecting a peak position.

Specifically, as shown in FIG. 12, let it be assumed that the image sensor 12, 21 is constituted of sixteen pixels in a row and twelve pixels in a column, wherein horizontal pixel arrays in a horizontal direction are expressed as h1, h2, h3, . . . , and h11, and vertical pixel arrays in a vertical direction are expressed as d1, d2, d3 . . . , and d16.

Then, the sum of the output values of the pixels belonging to each of the horizontal pixel arrays h1 to h12 is calculated to detect a maximal sum among the sums concerning the horizontal pixel arrays. Now, let it be assumed that, as shown by the arrow A in FIG. 12, the sum of the output values of the pixels in the horizontal pixel array h5 is maximal among the sums concerning the horizontal pixel arrays. Likewise, the sum of the output values of the pixels belonging to each of the vertical pixel arrays d1 to d16 is calculated to detect a maximal sum among the sums concerning the vertical pixel arrays. Now, let it be assumed that, as shown by the arrow B in FIG. 12, the sum of the output values of the pixels in the vertical pixel array d8 is maximal among the sums concerning the vertical pixel arrays.

Then, the position of the pixel that belongs both to the horizontal pixel array whose sum of the output values of the pixels is judged to be maximal, and to the vertical pixel array whose sum of the output values of the pixels is judged to be maximal is defined as the peak position. For instance, in the example of FIG. 12, the position of the pixel indicated by the arrow C, which belongs both to the horizontal pixel array h5 and to the vertical pixel array d8, is obtained as the peak position.

The aforementioned detection method is advantageous, as compared with the method described in the embodiment, in eliminating the need of comparison among output values from multitudes of pixels, thereby contributing to shortening of the processing time required for obtaining the peak position.

(2) In the embodiment, the area sensor having two-dimensionally arranged pixels is used as the image sensor 12, 21. Alternatively, a line sensor having one-dimensionally arranged pixels may be used. In the modification, two-dimensional light receiving data may be obtained by allowing the line sensor to perform an imaging operation while moving the line sensor in a direction orthogonal to the pixel array direction. Further alternatively, a spot-like sensor provided with a significantly small light receiving area may be used. In the latter modification, two-dimensional light receiving data may be obtained by allowing the sensor to perform an imaging operation while moving the sensor in two-dimensional directions.

(3) The number and the installation sites of the light sources and the image sensors are not limited to the arrangement of the embodiment, but may be modified as shown below.

Figure 13:
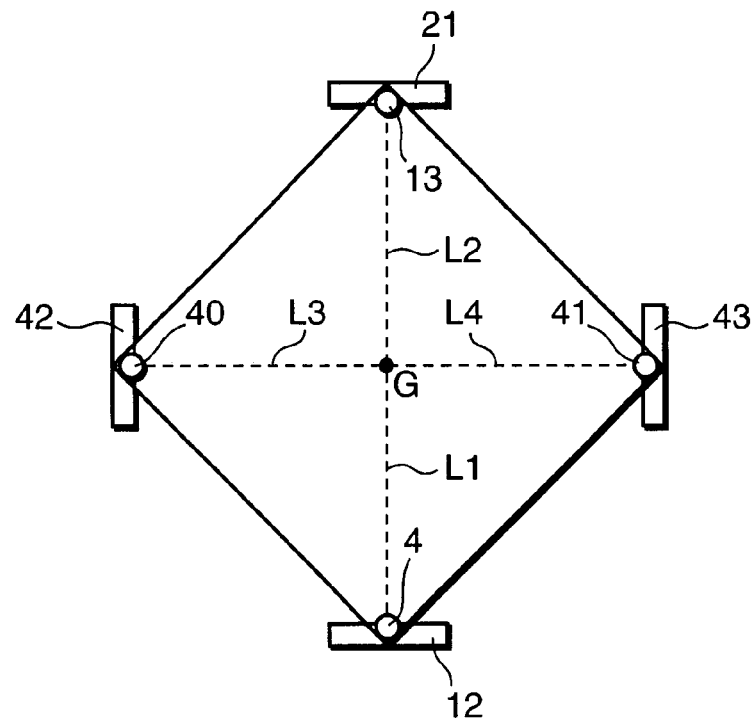
FIGS. 13 through 17 are diagrams showing modified arrangements on positional relations between light sources and image sensors.

(3-1) FIG. 13 is a diagram viewed from the direction of the normal G, showing that, assuming that the first and the second light projecting/detecting units 2 and 3 shown in FIG. 1 constitute an optical unit as a first optical unit, another optical unit as a second optical unit is provided in a direction perpendicular to the plane of FIG. 1 in addition to the arrangement shown in FIG. 1 which is constituted merely of the first optical unit.

Specifically, the first optical unit corresponds to light sources 4 and 13, and image sensors 12 and 21 shown in FIG. 13. The second optical unit corresponds to light sources 40 and 41, and image sensors 42 and 43. Assuming an imaginary plane orthogonal to the normal G, orthogonal projections of optical axes L3 and L4 of the second optical unit onto the plane are substantially orthogonal to orthogonal projections of the optical axes L1 and L2 of the first optical unit onto the plane. The light sources 40, 41 and the like are arranged based on the orthogonal relations between the optical axes L1 and L2, and the optical axes L3 and L4. Also, the image sensor 43 for receiving reflected light from the sample surface S illuminated with light outputted from the light source 40, and the image sensor 42 for receiving reflected light from the sample surface S illuminated with light outputted from the light source 41 are arranged at respective predetermined positions in the similar manner as the image sensors 12 and 21 shown in FIG. 1.

In the above arrangement, a measurement error resulting from a change in the setting position of the sample surface S can be eliminated or suppressed, in the case where the setting position of the sample surface S is changed from the proper position in forward or backward direction on the plane of FIG. 1, as well as in leftward or rightward direction on the plane of FIG. 1, by using the light receiving data obtained from the image sensors 42 and 43 in the similar manner as the embodiment. Alternatively, three or more optical units may be provided, in place of the two optical units. Further alternatively, in the case where light sources are provided in association with image sensors, weighting factors to be applied to the light receiving data obtained from the image sensors may be identical to each other.

(3-2) In the case where plural light sources are provided, the light sources are arranged opposed to each other with respect to the normal G in the embodiment or the arrangement shown in FIG. 13. In view of this, the optical axes of the reflected light from the half mirrors are bent by about 90° to eliminate interference with the optical paths of the light outputted from the light sources. Alternatively, in the case where the light sources are arranged at such position as not to oppose each other with respect to the normal G, the image sensors may be arranged at such positions as opposing the light sources with respect to the normal G. This is advantageous in omitting use of half mirrors.

Figure 14:
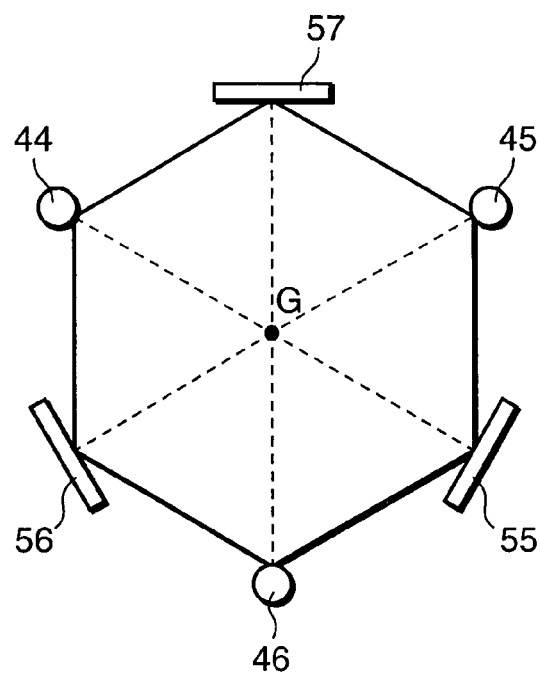

For instance, as shown in FIG. 14, in the case where three light sources 44, 45, and 46 are equidistantly arranged at such positions as not to oppose each other along a common circumference about the normal G as a center on a plane orthogonal to the normal G, image sensors 55, 56, and 57 for receiving reflected light from the sample surface illuminated with light outputted from the light sources 44, 45, and 46 may be arranged at such positions as opposing the respective corresponding light sources with respect to the normal G.

In the modification, assuming that a light source and an image sensor opposed to each other constitute a light projecting/detecting pair, and an imaginary plane orthogonal to the normal G is defined, as shown by the dotted line in FIG. 14, orthogonal projections of optical axes of the light projecting/detecting pair intersect with adjacent orthogonal projections by about 60°.

The number of pairs of the light sources (including optical components corresponding to the light diffusion plate 5, the restricting plate 6, the first lens element 7, the diaphragm 8, and the second lens element 10), and the image sensors is not limited to three as shown in FIG. 14. In the modification, the weighting factors to be applied to the light receiving data obtained from the image sensors may be identical to each other, because the light sources are provided in correspondence to the image sensors.

Figure 15:
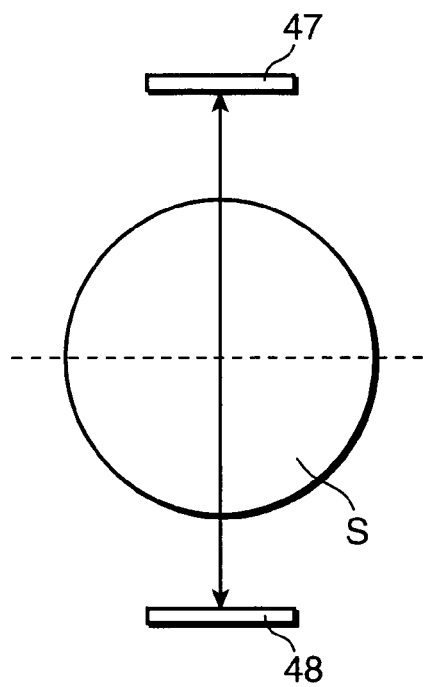
Figure 16:
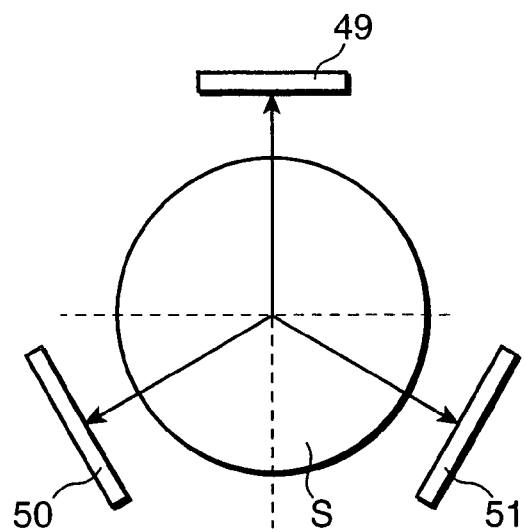

(3-3) FIGS. 15 and 16 are diagrams showing arrangements, wherein a single light source is provided on the normal G to the sample surface S shown in FIG. 1, the light source is caused to output light along the normal G, and plural image sensors are arranged axially symmetrically with each other with respect to the normal G.

FIG. 15 shows an arrangement, in which two image sensors 47 and 48 are arranged opposed to each other with respect to the normal G on a plane orthogonal to the normal G. FIG. 16 shows an arrangement, in which three image sensors 49, 50, and 51 are arranged equidistantly along a common circumference about the normal G as a center on the plane orthogonal to the normal G.

In the modification, even if a peak value is detected from one of the light receiving data, a peak value is not detected from the other light receiving data. Accordingly, a change in the specular reflection light component resulting from a change in the setting position of the sample surface S cannot be cancelled. Therefore, it is concluded that the modified arrangement is suitable to measure a sample surface S having a relatively small degree of gloss. In the modification, by applying the process to be executed by the reflection characteristic calculator 32 in the case where a peak value is not detected, as implemented in the embodiment, a measurement error resulting from inclination of the sample surface S can be eliminated or suppressed, thereby enabling to accurately obtain a characteristic of the sample surface S. In the case where the image sensors are arranged axially symmetrically with each other with respect to the normal G, the weighting factors to be applied to the light receiving data obtained from the image sensors may be identical to each other.

(3-4) In the case where the image sensors are axially asymmetrically arranged with respect to the normal G, the weighting factors to be applied to the light receiving data obtained from the image sensors may be set depending on the arranged positions of the image sensors, and a reflection characteristic of the sample surface S may be measured, considering the weighting factors.

Figure 17:
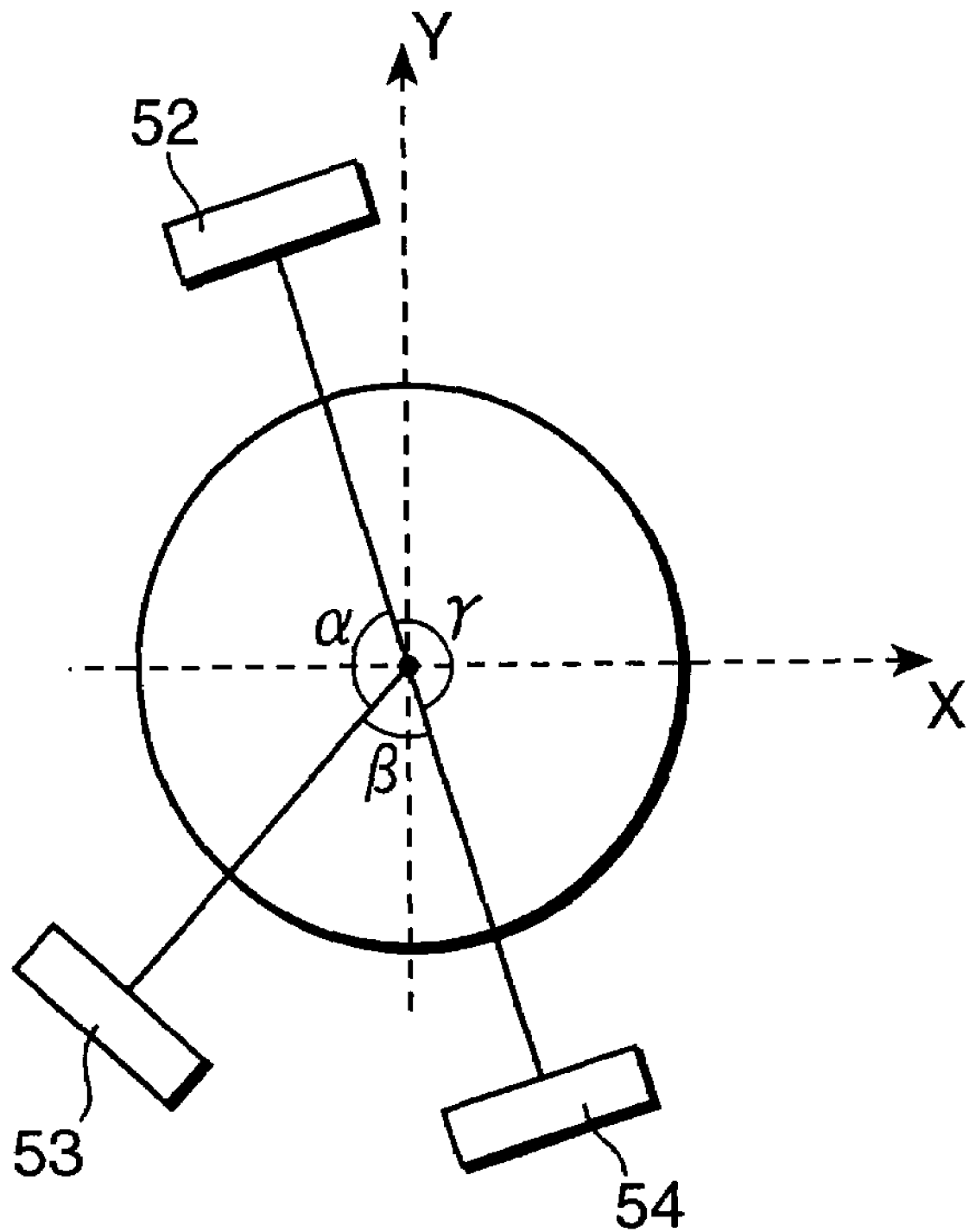
Figure 18:
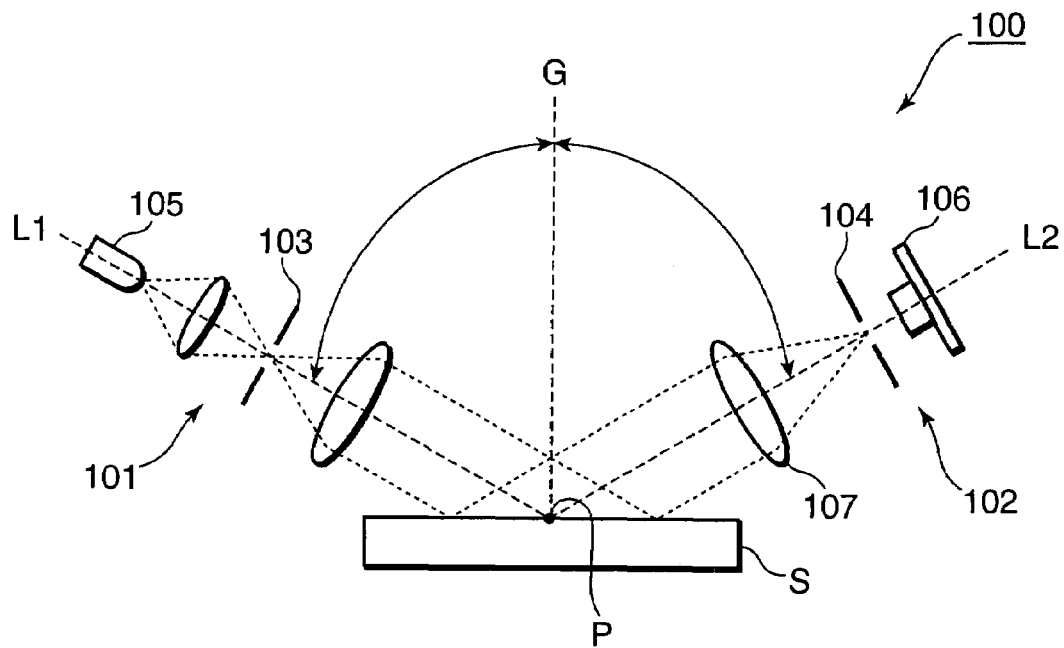
FIG. 18 is a diagram showing a reflection characteristic measuring apparatus according to a conventional art.
Figure 19:
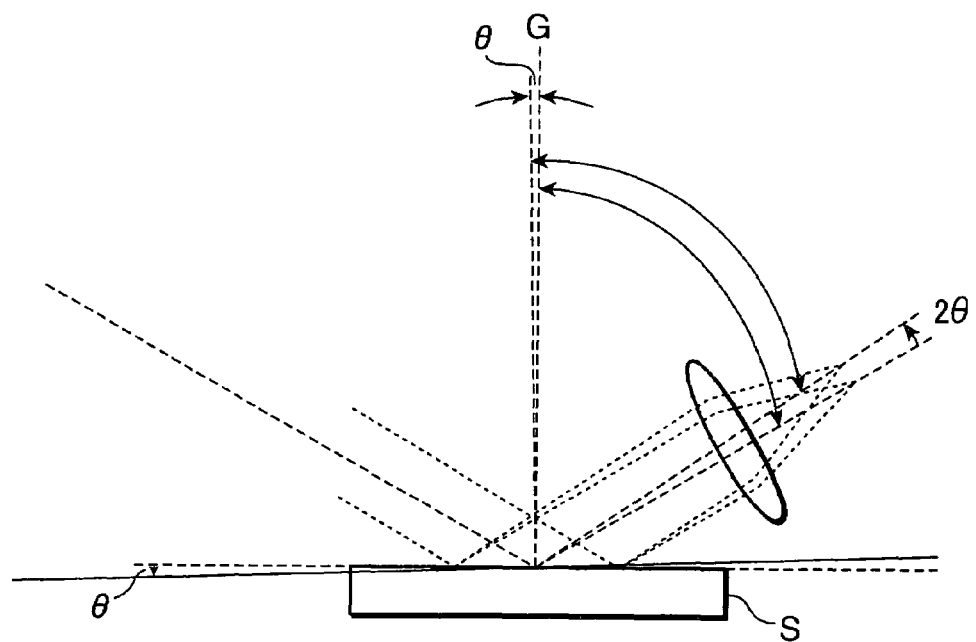
FIGS. 19 through 21B are diagrams for describing drawbacks in the conventional art.
Figure 20:
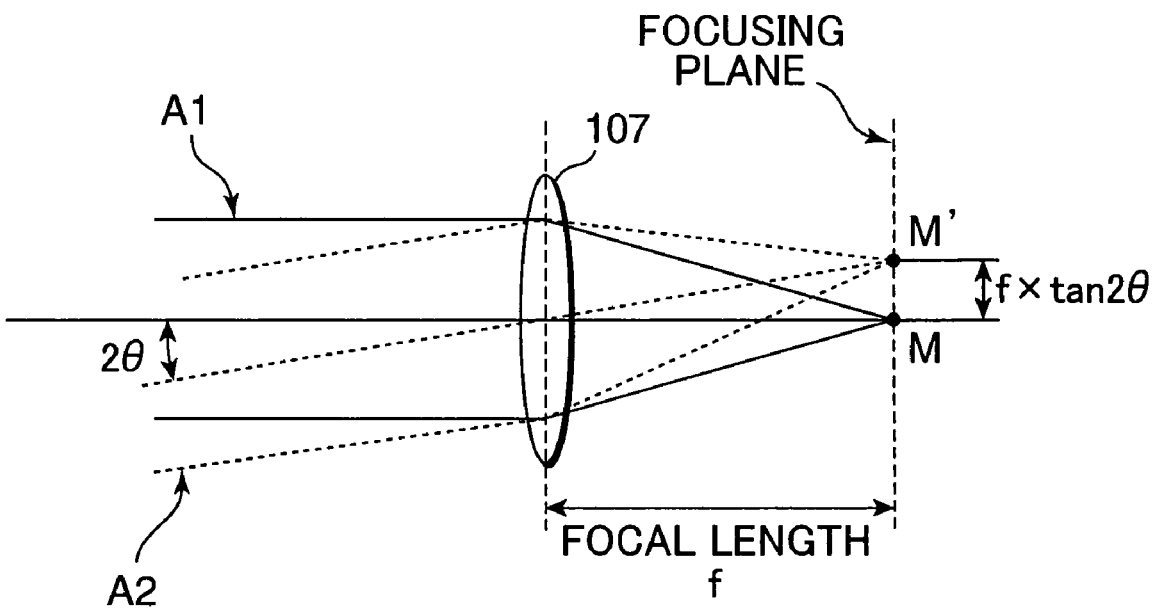
Figure 21A:
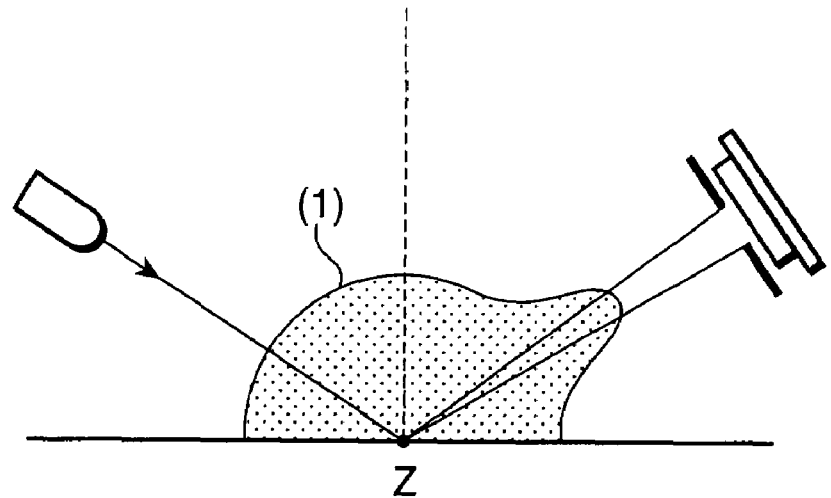
Figure 21B:
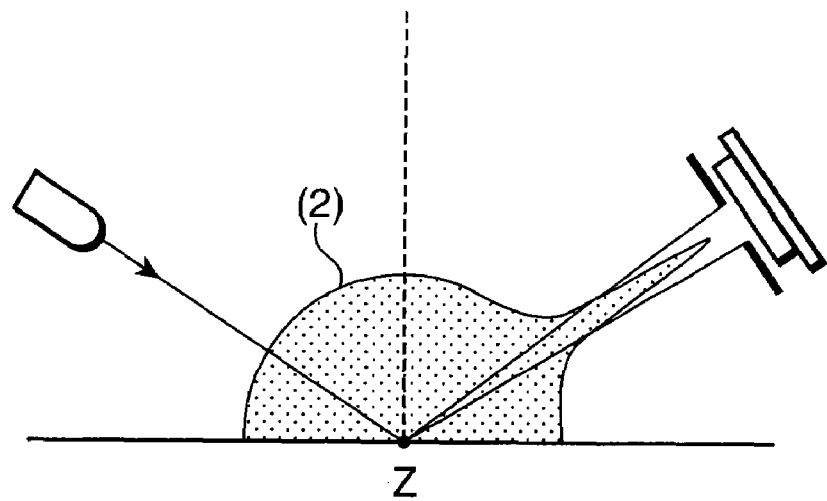

For instance, as shown in FIG. 17, in the case where three image sensors 52, 53, and 54 are arranged un-equidistantly along a common circumference about the normal G as a center on a plane orthogonal to the normal G, in other words, the angle α≠angle β≠angle γ, angle α≠angle γ, let it be considered a case of suppressing a measurement error resulting from inclination i.e. angular displacement of the sample surface S in a rotating direction about two axes orthogonal to the normal G i.e. X-axis and Y-axis.

In the above case, similarly to the modification (3-3), even if a peak value is detected from one of the light receiving data, a peak value is not detected from the other of the light receiving data. Accordingly, it is impossible to cancel a change in the specular reflection light component resulting from a change in the setting position of the sample surface S. Therefore, it can be concluded that the above arrangement is suitable to measure a sample surface S having a relatively small degree of gloss. By applying the process to be executed by the reflection characteristic calculator 32 in the case where a peak value is not detected, as implemented in the embodiment, a measurement error resulting from a change in the setting position of the sample surface S can be eliminated or suppressed, thereby enabling to accurately measure a characteristic of the sample surface S.

In the above arrangement, a weighting factor is applied to light receiving data corresponding to a predetermined area including the center position of the light receiving surface of each of the image sensors 52, 53, and 54 as a reference position, depending on the angles $\alpha$, $\beta$, and $\gamma$ with respect to each of the directions corresponding to the X-axis and the Y-axis. Then, an average of the light receiving data considering the weighting factors is calculated in each of the directions to eliminate or suppress a measurement error in each of the directions. This enables to accurately measure a reflection characteristic of the sample surface S, even if the image sensors are arranged axially asymmetrically with respect to the normal G.

Further, as shown in the aforementioned modification (3-3) and the present modification (3-4), in which the single light source is arranged on the normal G shown in FIG. 1, the light source is caused to output light along the normal G, and the plural image sensors are arranged axially symmetrically each other with respect to the normal G, the production cost can be suppressed, because the number of light sources is reduced, as compared with an arrangement that light sources are arranged in correspondence to image sensors.

(4) The dimensions of the area to be used in calculating the degree of gloss i.e. an angular area for obtaining the degree of gloss may be changed. In the modified arrangement, in the case where sample surfaces to be measured have different ratios of specular reflection light component to diffusion light component i.e. different reflection characteristics, but have identical degrees of gloss, by changing the dimensions of the pixel area for trimming, a difference in sum of the output values from the pixels belonging to the pixel areas before and after the change of the dimensions of the pixel area can be confirmed. This enables to distinguish the samples surface having the different reflection characteristics one from the other.

The foregoing embodiment and/or modifications primarily include the inventions having the following arrangements.

A reflection characteristic measuring apparatus according to an aspect of the invention includes: at least one illuminator for illuminating a sample surface to be measured with light; a plurality of light receiving sections each adapted for receiving the light reflected on the sample surface illuminated by the light from the illuminator to output two-dimensional light receiving data, respectively; and a deriving section for deriving a characteristic of the sample surface based on a weighted average obtained by applying a weighting factor to each of the light receiving data outputted from the light receiving sections based on an installation condition concerning the illuminator and the light receiving sections, and by averaging the light receiving data weighted with the weighting factors.

In the above arrangement, the light receiving sections are arranged at different positions to receive the light reflected on the sample surface illuminated with the light from the illuminator. In this arrangement, if the setting position of the sample surface is changed from a proper position, one of the light receiving sections is allowed to obtain light receiving data having an increased output value, as compared with a condition that the sample surface is set in the proper position, and the other one of the light receiving sections is allowed to obtain light receiving data having a decreased output value, as compared with the condition that the sample surface is set in the proper position.

In the above arrangement, the characteristic of the sample surface is obtained by applying the weighting factors to the respective light receiving data based on the installation condition concerning the illuminator and the light receiving sections, and based on the weighted average obtained by averaging the light receiving data applied with the weighting factors. Thereby, a measurement error included in the data representing the characteristic of the sample surface can be reduced, as compared with a measurement error concerning light receiving data to be obtained in an arrangement that a single light receiving section is provided. This enables to accurately measure the gloss of the sample surface, even if the setting position of the sample surface is changed.

Preferably, the reflection characteristic measuring apparatus may include: a first light projecting/detecting unit having one of the illuminators and one of the light receiving sections; and a second light projecting/detecting unit having the other one of the illuminators and the other one of the light receiving sections, and the illuminator of the first light projecting/detecting unit and the illuminator of the second light projecting/detecting unit may be arranged axially symmetrically with each other with respect to a normal to the sample surface set in a proper position at a certain point on a measurement area.

In the above arrangement, since the illuminator of the first light projecting/detecting unit and the illuminator of the second light projecting/detecting unit are arranged axially symmetrically with each other with respect to the normal, the weighting factors to be applied to the respective light receiving data obtained from the light receiving sections can be made identical to each other. This enables to simplify the weighted averaging computation, and to facilitate designing a program or a circuit for the computation.

Preferably, one of the first light projecting/detecting unit and the second light projecting/detecting unit may include: a light source; a lens element for guiding first light outputted from the light source to the sample surface; a light receiving sensor having a two-dimensional light receiving surface; and a half mirror for transmitting the first light, and for reflecting second light outputted from the light source of the other one and reflected on the sample surface to the light receiving surface of the light receiving sensor.

Preferably, plural optical units, each of which is constituted with the first light projecting/detecting unit and the second light projecting/detecting unit may be provided.

Preferably, the optical unit may include a first optical unit and a second optical unit, and the first optical unit and the second optical unit may be arranged at such positions that projections of optical axes of the first and second optical units onto a plane orthogonal to the normal are orthogonal to each other.

In the case where a single optical unit is provided, a measurement error concerning the light receiving data resulting from inclination of the sample surface is reduced merely in one direction. If, however, the plural optical units are provided, a measurement error concerning the light receiving data resulting from inclination of the sample surface can be reduced in plural directions. In the case where the single optical unit is provided, however, a measurement error concerning the light receiving data resulting from inclination of the sample surface can be reduced at least in one direction, and the number of illuminators can be reduced, as compared with the arrangement that the plural optical units are provided. Thus, the arrangement is advantageous in suppressing the production cost.

Preferably, the deriving section may be operative to: detect whether the respective light receiving data include a peak value; extract light receiving data belonging to a predetermined area defined with a position of the detected peak value as a reference position, out of the light receiving data obtained from the light receiving sections, if the peak value is detected; and derive the characteristic of the sample surface based on the weighted average of the extracted light receiving data.

Generally, light receiving data includes a peak value with respect to specular reflection light. In the above arrangement, if the peak value is detected, the light receiving data belonging to the predetermined area including the position corresponding to the detected peak value as the reference position is extracted, out of the light receiving data obtained from the light receiving sections, with respect to each of the light receiving data. This enables to obtain light receiving data including a specular reflection light component and a diffusion light component. Then, a measurement error concerning light receiving data having an increased output value and light receiving data having a decreased output value with respect to the specular reflection light component and the diffusion light component can be cancelled or suppressed by obtaining a weighted average concerning the light receiving data having the increased output value, which has been outputted from one of the light receiving sections, and the light receiving data having the decreased output value, which has been outputted from the other one of the light receiving sections, as compared with a condition that the sample surface is set in the proper position. This enables to accurately obtain the characteristic of the sample surface, even if the setting position of the sample surface is changed from the proper position.

Preferably, the illuminator may illuminate the sample surface with the light in a direction of a normal to the sample surface set in a proper position at a certain point on a measurement area, and the light receiving sections may be arranged axially symmetrically with each other with respect to the normal.

In the above arrangement, the illuminator illuminates the sample surface with the light in the direction of the normal when the sample surface is set in the proper position, and the light receiving sections receive the light at the axially symmetrical positions with each other with respect to the normal. This enables to suppress the cost, as compared with an arrangement that plural illuminators are provided.

Preferably, the deriving section may be operative to: detect whether the respective light receiving data include a peak value; extract light receiving data belonging to a predetermined area defined with a center position of the light receiving surface of each of the light receiving sections as a reference position, if the peak value is not detected; and derive the characteristic of the sample surface based on a weighted average of the extracted light receiving data.

The above arrangement enables to obtain the characteristic of the sample surface in the case where the peak value is not detected.

Preferably, the characteristic of the sample surface may be a characteristic relating to a gloss of the sample surface.

A reflection characteristic measuring apparatus according to another aspect of the invention includes: a first optical system having a first illuminator for illuminating a sample surface to be measured with light, a first condenser lens, and a first light receiving sensor, having two-dimensionally arranged pixels, for receiving the light reflected on the sample surface illuminated with the light from the first illuminator; a second optical system having a second illuminator for illuminating the sample surface with light, a second condenser lens, and a second light receiving sensor, having two-dimensionally arranged pixels, for receiving the light reflected on the sample surface illuminated with the light from the second illuminator; and a deriving section for deriving a characteristic of the sample surface, based on an average of first light receiving data outputted from the first light receiving sensor and second light receiving data outputted from the second light receiving sensor, wherein an optical axis of the first optical system and an optical axis of the second optical system are respectively arranged axially symmetrically with respect to a normal to the sample surface set in a proper position at a certain point on a measurement area, and the first optical system and the second optical system are arranged at such positions that the optical axis of the first optical system and the optical axis of the second optical system are at least closely identical to each other to cancel a change of the first light receiving data by a change of the second light receiving data, if a position of the sample surface changes from the proper position.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A reflection characteristic measuring apparatus, comprising:
   a first light projecting/detecting unit having an illuminator and a light receiving section;
   a second light projecting/detecting unit having another illuminator and another light receiving section;
   said illuminators configured to illuminate a sample surface to be measured with light;
   said light receiving sections each adapted for receiving the light reflected on the sample surface illuminated by the light from the respective illuminator to output two-dimensional light receiving data, said light receiving sections being arranged axially symmetrically with each other with respect to a normal to the sample surface set in a predetermined position at a point on a measurement area; and
   a processor configured to derive a characteristic of the sample surface based on a weighted average obtained by applying a weighting factor to each of the light receiving data outputted from the light receiving sections based on an installation condition concerning the illuminator and the light receiving sections, and by averaging the light receiving data weighted with the weighting factors,
   wherein
   one of the first light projecting/detecting unit and the second light projecting/detecting unit includes:
   a light source;
   a lens element configured to guide first light outputted from the light source to the sample surface;
   a light receiving sensor having a two-dimensional light receiving surface; and a half mirror configured to transmit the first light from the light source of the one of the first light projecting/detecting unit and the second light projecting/detecting unit, and for reflecting second light outputted from a light source of the other one of the first light projecting/detecting unit and the second light projecting/detecting unit that has been reflected on the sample surface to the light receiving surface of the light receiving sensor.

2. The reflection characteristic measuring apparatus according to claim 1, wherein
plural optical units, each of which is constituted with the first light projecting/detecting unit and the second light projecting/detecting unit are provided.

3. The reflection characteristic measuring apparatus according to claim 2, wherein
the optical unit includes a first optical unit and a second optical unit, and
the first optical unit and the second optical unit are arranged at such positions that projections of optical axes of the first and second optical units onto a plane orthogonal to the normal are orthogonal to each other.

4. The reflection characteristic measuring apparatus according to claim 1, wherein
the deriving section is operative to:
detect whether the respective light receiving data include a peak value;
extract light receiving data belonging to a predetermined area defined with a position of the detected peak value as a reference position, out of the light receiving data obtained from the light receiving sections, if the peak value is detected; and
derive the characteristic of the sample surface based on the weighted average of the extracted light receiving data.

5. The reflection characteristic measuring apparatus according to claim 1, wherein
the illuminator illuminates the sample surface with the light in a direction of a normal to the sample surface set in a predetermined position at a point on a measurement area, and
the light receiving sections are arranged axially symmetrically with each other with respect to the normal.

6. The reflection characteristic measuring apparatus according to claim 1, wherein
the processor is operative to:
detect whether the respective light receiving data include a peak value;
extract light receiving data belonging to a predetermined area defined with a center position of the light receiving surface of each of the light receiving sections as a reference position, if the peak value is not detected; and
derive the characteristic of the sample surface based on a weighted average of the extracted light receiving data.

7. The reflection characteristic measuring apparatus according to claim 1, wherein
the characteristic of the sample surface is a characteristic relating to a gloss of the sample surface.

8. The reflection characteristic measuring apparatus according to claim 1, wherein the optical axes of the plurality of light receiving sections are arranged axially symmetrically with each other with respect to a normal to the sample surface set in a predetermined position at a point on a measurement area.

9. A reflection characteristic measuring apparatus, comprising:
a first optical system including
a first illuminator configured to illuminate a sample surface to be measured with light,
a first condenser lens, and
a first light receiving sensor, having two-dimensionally arranged pixels, for receiving the light reflected on the sample surface illuminated with the light from the first illuminator;
a second optical system including
a second illuminator configured to illuminate the sample surface with light,
a second condenser lens, and
a second light receiving sensor, having two-dimensionally arranged pixels, for receiving the light reflected on the sample surface illuminated with the light from the second illuminator; and
a processor configured to derive a characteristic of the sample surface, based on an average of first light receiving data outputted from the first light receiving sensor and second light receiving data outputted from the second light receiving sensor, wherein
an optical axis of the first optical system and an optical axis of the second optical system are respectively arranged axially symmetrically with respect to a normal to the sample surface set in a predetermined position at a point on a measurement area, and
the first optical system and the second optical system are arranged at such positions that the optical axis of the first optical system and the optical axis of the second optical system are substantially identical to each other so as to cancel a change of the first light receiving data by a change of the second light receiving data, if a position of the sample surface changes from the predetermined position.

10. The reflection characteristic measuring apparatus according to claim 9, wherein
the processor is operative to:
detect whether each of the first light receiving data and the second light receiving data includes a peak value;
extract light receiving data belonging to a predetermined area defined with a position of the detected peak value as a reference position, out of the first light receiving data and the second light receiving data, if the peak value is detected; and
derive the characteristic of the sample surface based on a weighted average of the extracted light receiving data.

11. A reflection characteristic measuring apparatus, comprising:
a first optical system including:
a first illuminator configured to illuminate with light a portion of sample surface to be measured,
a first condenser lens, and
a first light receiving sensor, having two-dimensionally arranged pixels, for receiving the light reflected on the portion of sample surface illuminated with the light from the second illuminator;
a second optical system including
a second illuminator configured to illuminate with light substantially the same portion of the sample surface illuminated by the first illuminator,
a second condenser lens, and
a second light receiving sensor, having two-dimensionally arranged pixels, for receiving the light reflected on the portion of the sample surface illuminated with the light from the first illuminator; and a processor configured to derive a characteristic of the portion of the sample surface based on light receiving data outputted from the first light and second light receiving sensors, wherein the first optical system and the second optical system are arranged at respective positions and are arranged relative to an intended position of a sample to be measured so that at least a first portion of a first optical axis of the first optical system for providing light from the first illuminator to a sample to be measured is the same as a first portion of the first optical axis of the first optical system for receiving light for the first light receiving sensor and at least a second portion of a second optical axis of a second optical system for providing light from the second illuminator to a sample to be measured is the same as the second portion of the second optical axis of the second optical system from receiving light for the second light receiving sensor, and wherein receiving sensors, and an optical axis of the first optical system and an optical axis of the second optical system are respectively arranged axially symmetrically with respect to a normal to the sample surface set in a predetermined position at a point on a measurement area.

12. A reflection characteristic measuring apparatus, comprising:

a first light projecting/detecting unit having an illuminator and a light receiving section;

a second light projecting/detecting unit having another illuminator and another light receiving section;

said illuminators configured to illuminate a sample surface to be measured with light;

said light receiving sections each adapted for receiving the light reflected on the sample surface illuminated by the light from the respective illuminator to output two-dimensional light receiving data, wherein optical axes of the reflected light to be incident to the plurality of light receiving sections being arranged axially symmetrically with each other with respect to a normal to the sample surface set in a predetermined position at a point on a measurement area; and a processor configured to derive a characteristic of the sample surface based on a weighted average obtained by applying a weighting factor to each of the light receiving data outputted from the light receiving sections based on an installation condition concerning the illuminator and the light receiving sections, and by averaging the light receiving data weighted with the weighting factors, wherein one of the first light projecting/detecting unit and the second light projecting/detecting unit includes:

a light source;

a lens element configured to guide first light outputted from the light source to the sample surface;

a light receiving sensor having a two-dimensional light receiving surface; and a half mirror configured to transmit the first light from the light source of the one of the first light projecting/detecting unit and the second light projecting/detecting unit, and for reflecting second light outputted from a light source of the other one of the first light projecting/detecting unit and the second light projecting/detecting unit that has been reflected on the sample surface to the light receiving surface of the light receiving sensor.

* * * * *

UNITED STATES PATENT AND TRADEMARK OFFICE
CERTIFICATE OF CORRECTION

| | | |
|---|---|---|
| PATENT NO. | : 7,719,687 B2 | Page 1 of 2 |
| APPLICATION NO. | : 11/805486 | |
| DATED | : May 18, 2010 | |
| INVENTOR(S) | : Jun Matsumoto, Kenji Imura and Yoshihiro Okui | |

It is certified that error appears in the above-identified patent and that said Letters Patent is hereby corrected as shown below:

Column 21:
Line 25, claim 4, delete "deriving section" and insert -- processor --.

Column 23:
Lines 7-21, claim 11, delete "the first optical system and the second optical system are arranged at respective positions and are arranged relative to an intended position of a sample to be measured so that at least a first portion of a first optical axis of the first optical system for providing light from the first illuminator to a sample to be measured is the same as a first portion of the first optical axis of the first optical system for receiving light from the first light receiving sensor and at least a second portion of a second optical axis of a second optical system for providing light from the second illuminator to a sample to be measured is the same as the second portion of the second optical axis of the second optical system for receiving light for the second light receiving sensor, and wherein receiving sensors,".

Column 23:
Lines 7-21, claim 11, insert -- the first optical system and the second optical system are arranged at respective positions and are arranged relative to an intended position of a sample to be measured so that when a reflection characteristic of a sample is measured, light from the first illuminator impinges on and reflects off the portion of the sample and such light is received by the second optical system so as to be sensed by the second light receiving sensor, and light from the second illuminator impinges on and reflects off the portion of the sample and such light is received by the first optical system so as to be sensed by the first light receiving sensor,
  at least a first portion of a first optical axis of the first optical system for providing light from the first illuminator to a sample to be measured is the same as a first portion of the first optical axis of the first optical system for receiving light from the first light receiving sensor and at least a second portion of a second optical axis of a second optical system for providing light from the second illuminator to a sample to be measured is the same as the second portion of the second optical axis of the second optical system for receiving light for the second light receiving sensor, and wherein Signed and Sealed this Thirteenth Day of July, 2010

David J. Kappos
*Director of the United States Patent and Trademark Office* the processor is configured to derive a characteristic of the sample surface based on an average of the light receiving data outputted from the first and second light receiving sensors, --.